US008034349B2

(12) United States Patent
Teti et al.

(10) Patent No.: US 8,034,349 B2
(45) Date of Patent: Oct. 11, 2011

(54) PEPTIDES THAT MIMIC NON-HUMAN CROSS-REACTIVE PROTECTIVE EPITOPES OF THE GROUP B MENINGOCOCCAL CAPSULAR POLYSACCHARIDE

(75) Inventors: Giuseppe Teti, Messina (IT); Franco Felici, Messina (IT)

(73) Assignees: Giuseppe Teti, Messina (IT); Franco Felici, Messina (IT)

( * ) Notice: Subject to any disclaimer, the term of this patent is extended or adjusted under 35 U.S.C. 154(b) by 298 days.

(21) Appl. No.: 12/304,989

(22) PCT Filed: Jun. 12, 2007

(86) PCT No.: PCT/IB2007/002668

§ 371 (c)(1), (2), (4) Date: Mar. 25, 2009

(87) PCT Pub. No.: WO2007/144771

PCT Pub. Date: Dec. 21, 2007

(65) Prior Publication Data

US 2010/0068219 A1 Mar. 18, 2010

(30) Foreign Application Priority Data

Jun. 15, 2006 (GB) .................................. 0611914.3

(51) Int. Cl.

| | |
|---|---|
| *A61K 39/00* | (2006.01) |
| *A61K 39/02* | (2006.01) |
| *A61K 39/095* | (2006.01) |
| *A61K 48/00* | (2006.01) |
| *C07H 21/04* | (2006.01) |
| *C07K 1/00* | (2006.01) |
| *C07K 2/00* | (2006.01) |

(52) U.S. Cl. ............... 424/185.1; 424/190.1; 424/234.1; 424/250.1; 514/44 R; 530/300; 530/350; 536/23.7

(58) Field of Classification Search ........................ None
See application file for complete search history.

(56) References Cited

U.S. PATENT DOCUMENTS

| | | | | |
|---|---|---|---|---|
| 4,356,170 | A | 10/1982 | Jennings et al. | |
| 4,727,136 | A | 2/1988 | Jennings et al. | |
| 4,970,070 | A | 11/1990 | Raff | |
| 5,576,002 | A | 11/1996 | Jennings et al. | |
| 5,683,699 | A | 11/1997 | Jennings et al. | |
| 5,811,102 | A | 9/1998 | Jennings et al. | |
| 5,902,586 | A | 5/1999 | Jennings et al. | |
| 5,969,130 | A | 10/1999 | Jennings et al. | |
| 6,030,619 | A | 2/2000 | Granoff et al. | |
| 6,048,527 | A | 4/2000 | Granoff et al. | |
| 6,638,513 | B2 | 10/2003 | Seid | |
| 7,534,444 | B2 | 5/2009 | Granoff et al. | |
| 2004/0034888 | A1* | 2/2004 | Liu et al. | 800/289 |

FOREIGN PATENT DOCUMENTS

| | | | |
|---|---|---|---|
| EP | 0145359 | A2 | 6/1985 |
| EP | 0504202 | B1 | 5/1995 |
| SU | 1708846 | A1 | 1/1992 |
| WO | WO-90/06696 | | 6/1990 |
| WO | WO-91/06772 | | 6/1991 |
| WO | WO-95/14085 | | 5/1995 |
| WO | WO-98/05543 | | 3/1998 |
| WO | WO-2007/073706 | | 7/2007 |
| WO | WO 2007/073706 | | 7/2007 |

OTHER PUBLICATIONS

Moe, G. et al. "Molecular mimetics of polysaccharide epitopes as vaccines candidates for prevention of *Neisseria meningitidis* serogroup B disease," FEMS, 26: 209-226 (1999).
Granoff, D. et al. "Bactericidal monoclonal antibodies that define unique meningococcal B polysaccharide epitopes that do . . . " Journal of Immunology, 160 (10):5028-5036 (1998).
Shin, J. et al. "Monoclonal antibodies specific for *Neisseria meningitidis* group B polysaccharide and their peptide mimotopes," Infect. Immun., 69 (5): 3335-3342 (2001).
Passo, C. et al. "Peptide mimics of the group B meningococcal capsule induce bactericidal and protective antibodies after . . . " Journal of Immunology, 178 (7): 4417-4423 (2007).
Ashton et al., "Protective efficacy of mouse serum to the N-propionyl derivative of meningococcal group B polysaccharide," *Microb. Patheogeneis* 6:455-458 (1989).
Ashton et al., "Immunological properties of monoclonal antibodies to the N-propionyl derivative of group B meningococcal polysaccharide," *In: Neisseria 1990, Achtman M. (Ed. ), Walter De Gruyter & Co.* Berlin pp. 187-191 (1991).
Bartoloni et al., "Immunogenicity of meningococcal B polysaccharide conjugated to tetanus tosoid or CRM197 via adipic acid dihydrazide," *Vaccine* 13(5):463-470 (1995).
Baumann et al., "Comparison of the conformation of the epitope of alpha(2á8) polysialic acid with its reduced and N-acyl derivatives," *Biochemistry* 32:4007-4013 (1993).
Bitter-Suermann et al., "Monoclonal antibodies to polysialic acid reveal epitope sharing between invasive pathogenic bacteria, differentiating cells and tumor cells," *Immunol. Res.* 6(4):225-237 (1987).
Bowie et al., "Deciphering the message in protein sequences: Tolerance to amino acid substitutions," *Science* 247:1306-1310 (1990).
Brisson et al., "Helical Epitope of the Group B Meningococcal a92-B)-Linked Sialic Acid Polysaccharide," *Biochemistry* 31(21):4996-5004 (1992).
Burgess et al., (1990). "Possible dissociation of the heparin-binding and mitogenic activities of heparin-binding (acidic fibroblast) growth factor-1 from its receptor-binding activities by site-directed mutagenesis of a single lysine residue," *J. Cell Biol.* 111:2129-2138.
Cross et al., "Evaluation of immunotherapeutic approaches for the potential treatment of infections caused by K1-positive *Escherichia coli*," *J. Infect. Dis.* 147(1):68-76 (1983).

(Continued)

*Primary Examiner* — Albert Navarro
(74) *Attorney, Agent, or Firm* — Amy Hessler; Otis Littlefield; Robert Gorman

(57) ABSTRACT

Peptides that mimic the antigenic features of non human-cross-reactive protective epitopes of the MenB CP and nucleic acids encoding the peptide mimetics are disclosed. Antibodies elicited by these peptides do not bind to polysialic acid in host tissue and thus provide a safe and efficacious method for the treatment and/or prevention of Meningitis B.

15 Claims, 8 Drawing Sheets

OTHER PUBLICATIONS

Devi et al., "Binding diversity of monoclonal antibodies to alpha(2-8) polysialic acid conjugated to outer membrane vesicle via adipic acid dihydrazide," *FEMS Immunol. Med. Microbiol.* 11.:211-220 (1996).

Devi et al, (Mar. 1997). "Preclinical evaluation of group B *Neisseria meningitidis* and *Escherichia coli* K92 capsular polysaccharide-protein conjugate vaccines in juvenile rhesus monkeys," Infect Immun 65(3):1045-52.

Dubois et al., "A Monoclonal Antibody Against *Meningococcus* Group B Polysaccharides Used to Immunocapture and Quantify Polysialylated NCAM in Tissues and Biological Fluids," *Journal of Immunological Methods* 181:125-135 (1995).

Frasch, Carl E., "Meningococcal Vaccines: Past, Present and Future," *Meningococcal Disease* 245-283 (1995).

Frosch et al., "NZB mouse system for production of monoclonal antibodies to weak bacterial antigens: Isolation of an IgG antibody to the polysaccharide capsules of *Escherichia coli* K1 and group B meningococci," *PNAS* 82: 1194-1198 (1985).

Fusco et al., "Preclinical Evaluation of a Novel Group B Meningococcal Conjugate Vaccine that Elicits Bactericidal Activity in Both Mice and Nonhuman Primates," *The Journal of Infectious Disease* 175:364-372 (1997).

Granoff et al., "Antibody Responses to the Capsular Polysaccharide of *Neisseria menignitidis* Serogroup B in Patients With Meningococcal Disease," *Clinical and Diagnostic Laboratory Immunology* 2(5):574-582 (1995).

Gregson et al., "Monoclonal antibodies against meningococcal polysaccharide with cross-reactivity against brain antigens," *Biochem. Soc. Transact.* 13;p. 462 (1985).

Hayrinen et al., "Antibodies to Polysialic Acid and its N-Propyl Derivative: Binding Properties and Interaction with Human Embryonal Brain Glycopeptides," *The Journal Of Infectious Diseases* 171:1481-1490 (1995).

Horwell, David C. "The 'Peptoid' Approach to the Design of Non-Peptide, Small Molecule Agonist and Antagonists of Neuropeptides," *TIBTech* 13(4): 132-134 (1995).

Hurpin et al., "Bactericidal activity of two Ig2a murine monoclonal antibodies with disilnet fine specificities for group B *Neisseria meningitidis* capsular polysaccharide," *Hybridoma* 11(6):677-687 (1992).

Husmann et al., "Immunohistochemical localization of polysialic acid in tissue sections: differential binding to polynucleolides and DNA of a murine IgG and a human IgM monoclonal antibody," *J. Histochem Cytochem.* 38:209-215 (1990).

Jennings. Harold J., "The Capsular Polysaccharide of Group B *Neisseria meningitidis* as a Vehicle for Vaccine Development," *Microbiol. Immunol.* 10:151-165 (1989).

Jennings et al., "Induction of *Meningococcal* Group B Polysaccharide-Specific IgG Antibodies in Mice by Using an N-Propionylated B Polysaccharide-Tetanus Toxoid Conjugate Vaccine," *The J. of Immunology* 137(5):1708-1713 (1986).

Jennings et al., "N-Polysialic Group B Meningococcal Polysaccharide Mimic a Unique Epitope on Group B *Neisseria meningitidis*," *J. Experimental Medicine* 165: 1207-1211 (1987).

Jennings et al. "Unique Intermolecular Bactericidal Epitope Involving the Homosialopolysaccharide Capsule on the Cell Surface of Group B *Neisseria meningitidis* and *Escherichia coli* K1," *Journal of Immunology* 142(10):3585-3591 (1989).

Jennings et al., "Immunochemistry of Groups A,B, and C Meningococcal Polysaccharide-Tetanus Toxoid Cojugates," *The Journal of Immunology* 127(3):1011-1018 (1981).

Kabat et al., "A human monoclonal macroglobulin with specificity of alpha(2→8)-linked poly-N-acetyl neuraminic acid, the capsular polysaccharide of group B meningococci and *Eschericia coli* K1, which crossreacts with polynucleotides and with denatured DNA," *J. Exp. Med.* 164:642-654 (1986).

Klebert et al., "Primary structure of the murine monoclonal IgG2a antibody mAb735 against alpha (2-8) polysialic acid. 2. Amino acid sequence of the heavy (H–) chain Fd' region," *Biol. Chem. Hoppe Seyler* 374:993-1000 (1993).

Lazar et al., "Transforming growth factor alpha: mutation of aspartic acid 47 and leucine 48 results in different biological activities," *Mol. Cell Biol.* 8:1247-1252, 1988.

Leinonen et al., "Class-specific antibody response to group B *Neisseria meningitidis* capsular polysaccharide: use of polylysine precoating in an enzyme-linked immunosorbent assay," *Infect. Immun.* 38(3):1203-1207 (1982).

Lifely et al., "Specificity of the immune tosi)onse to the group B polysaccharide of *Neisseria meningitidis*," *Immunology* 74:490-496 (1991).

Livingston et al., "Extended polysialic acid chains (n greater than 55) in glycoproteins from human neuroblastoma cells," *J. Biol. Chem.* 253:9443-9448 (1988).

Lommatzsch et al., "Outer membrane localization of murein hydrolases: MltA, a third lipoprotein lytic transglycosylase in *Escherichia coli*," *J. Bacteriol.* 179:5465-5470 (1997).

Lucas et al., "Functionai Differences in Idiotypically Defined IgG 1 Anti-Polysaccharide Antibodies Elicited by Vaccination with *Haemophilus Influenzae* Type B Polysaccharide-Protein Conjugates," *The Journal of Immunology* 154:4195-4202 (1995).

Mandrell et al., "Complernent-Mediated Bactericidal Activity of Human Antibodies in Poly alpha 2→8 N-Acetylneurarninic Acid, the Capsular Polysaccharide of *Neisseria meningitidis* Serogroup B," *The Journal of Infectious Diseases* 172: 1279-1289 (1995).

Moreno et al., "Immunological properties of monoclonal antibodies specific for meningococcal polysaccharides: the protective capacity of IgM antibodies specific for polysaccharide group B," *J. Gen. Microbiol.* 129:2451-2456 (1983).

Michon et al., "Conformational Differences Between Linear a(2-8)-Linked Homosialooligosaccharides and the Epitope of the Group B Meningococcal Polysaccharide," *Biochemistry* 26:8399-8405 (1987).

Pizza et al., "Identification of vaccine candidates :against serogroup 8 Meningococcus by whole-genome sequencing," *Science* 287:1816-1820 (2000).

Pon et al., "N-propionylated group B meningococcal polysaccharide mimics a unique bacterial capsular epitope in group B *Neisseria meningitidis*," *J. Exp. Med.* 185:1929-1938 (1997).

Poolman, Jan T., "Development of a Meningococcal Vaccine," *Infectious Agents and Disease* 4:13-28 (1995).

Raff et al., "Human monoclonal antibody with protective activity for *Escherichia coli* K1 and *Neisseria meningitidis* group B infections," *J. Infect. Dis.* 157(1):118-126 (1988).

Rougon et al., "A monoclonal antibody against meningococcus group B polysaccharides distinguishes embryonic from adult N-CAM," *J. Cell. Biol.* 103:2429-2437 (1986).

Sato et al., "Characterization of the antigenic specificity of four different anti-(alpha2→8-Linked polysialic acid) antibodies using lipid-conjugated oligo/polysialic acids," *J. Biol. Chem.* 270:18923-18928 (1995).

Sukkonen et al., "Antibodies to the capsular polysaccharide of *Neisseria meningitidis* group B or *E. coli* K1 bind to the brains of infant rats in vitro but not in vivo," *Microbial. Pathogenesis* 1: 101-105 (1986).

Tettelin et al., "Complete genome sequence of *Neisseria meningitidis* serogroup B strain MC58," *Science* 287;1809-1815 (2000).

Tome et al., "Comparison of immunoreactivity between two different monoclonal antibodies recognizing peptide and polysialic acid chain epitopes on the neural cell adhesion molecule in normal tissues and lung tumors," *Acta Pathol. Jpn.* 43:168-175 (1993).

Vaesen et al., "Primary structure of the murine monoclonal IgG2a antibody mAb735 against alpha(2-8) polysialic acid. 1) Amino-acid sequence of the light (L–) chain, kappa-isotype," *Biol. Chem. Hoppe. Seyler* 372:451-453 (1993).

Westerink et al., "Development and Characterization of an Anti-Idiotype Antibody to the Capsular Polysaccharide of *Neisseria mengingitidis* Serogroup C," *Infection and Immunity* 56(5):1120-1127 (1988).

\* cited by examiner

US 8,034,349 B2

PEPTIDES THAT MIMIC NON-HUMAN CROSS-REACTIVE PROTECTIVE EPITOPES OF THE GROUP B MENINGOCOCCAL CAPSULAR POLYSACCHARIDE

All documents cited herein are incorporated by reference in their entirety.

TECHNICAL FIELD

This invention is in the field of bacterial pathogens, in particular the invention relates to peptides that elicit functional activity against *Neisseria meningitidis* serogroup B and also lack autoimmune activity. The invention also relates to methods of obtaining and using the peptides of the invention.

BACKGROUND ART

*Neisseria meningitidis*, is an encapsulated bacterium classified into different serogroups based on the chemical composition and immunologic features of the capsular polysaccharide (CP; 1). Human isolates are almost totally accounted for by 5 serogroups (A, B, C, Y and W135). No vaccine is generally available for the prevention of infections caused by serotype B strains, which often account for more that half of meningococcal disease cases in developed countries (2). Major obstacles to the development of capsule-based vaccines are the poor immunogenicity of the group B capsular polysaccharide (MenB CP) even after protein conjugation, and concerns over the induction of autoantibodies (3). These features are probably related to the structural identity between the *Neisseria meningitidis* group B capsular polysaccharide and human polysialic acid (PSA), both consisting of alpha 2-8 linked N-acetyl neuraminic acid. It is readily apparent that the production of a safe and effective vaccine against MenB would be particularly desirable. Studies using mAbs have defined two different classes of capsular epitopes naturally present on the meningococcal surface (4, 5, 6). One class is cross-reactive with human PSA, while the other is non-cross reactive and protective.

Therefore it is an object of the invention to provide further and improved immunogenic compositions for providing immunity against *Neisseria meningitidis*. It is a further object of the invention to provide peptides that mimic the antigenic features of capsular epitopes naturally present on the meningococcal surface which are both non-cross reactive and protective.

DISCLOSURE OF THE INVENTION

The inventors have identified peptides that mimic the antigenic features of MenB CP epitopes that are non-cross-reactive with human PSA ("non human-cross-reactive protective epitopes"). Thus the present invention relates to peptide mimetics of unique epitopes of MenB CP. Antibodies elicited by these peptides do not bind to polysialic acid in host tissue as determined by the autoreactivity assays described herein, and so they provide a safe and efficacious method for the prevention of MenB. Furthermore, the present invention relates to nucleic acids encoding the peptide mimetics of the present invention and methods of using them in nucleic acid immunization.

Accordingly, in one embodiment, the present invention relates to a molecular mimetic of an epitope of MenB, wherein said mimetic is a peptide which is non-cross-reactive with human PSA. The peptide may have an amino acid sequence selected from the group consisting of SEQ ID Nos 1-13.

In another embodiment, the present invention relates to nucleic acids encoding the polypeptides of the invention. Preferably, the present invention relates to nucleic acids selected from the group consisting of SEQ ID Nos 18-32.

In another embodiment, the invention relates to pharmaceutical compositions such as vaccines, comprising the polypeptides or nucleic acids of the present invention in admixture with a pharmaceutically acceptable carrier.

The invention also provides a method for protecting a patient from Men B infection, comprising administering to the patient a pharmaceutical composition of the invention.

In another embodiment, the present invention is directed to a polypeptide or nucleic acid of the present invention, for use in medicine.

In another embodiment, the present invention is directed to the use of a polypeptide or nucleic acid of the present invention, in the manufacture of a medicament for raising an immune response in a patient wherein the immune response is protective, for example, against Men B infection.

In another embodiment, the present invention is directed to the use of a nucleic acid of the present invention as a primer and the use of a polypeptide of the present invention as a booster, in the manufacture of a medicament for raising an immune response in a patient wherein the immune response is protective, for example, against Men B infection.

Polypeptides

Polypeptides of the invention may comprise the amino acid sequences SEQ ID NOs 1 to 13.

Preferred amino acid sequences from within SEQ ID NOs 1 to 13 are SEQ ID NO 1 and SEQ ID NO 3.

Polypeptides of the invention may comprise amino acid sequences that have sequence identity to the amino acid sequences disclosed in the examples. Depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more). These polypeptides include homologs, orthologs, allelic variants and mutants. Identity between polypeptides is preferably determined by the Smith-Waterman homology search algorithm as implemented in the MPSRCH program (Oxford Molecular), using an affine gap search with parameters gap open penalty=12 and gap extension penalty=1.

These polypeptides may, compared to SEQ ID No.s 1-13, include one or more (e.g. 1, 2, 3, 4, 5, 6, etc.) conservative amino acid substitutions i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. Moreover, the polypeptides may have one or more (e.g. 1, 2, 3, 4, 5, 6 etc.) single amino acid deletions relative to a reference sequence.

Furthermore, the polypeptides may include one or more (e.g. 1, 2, 3, 4, 5, 6 etc.) insertions (e.g. each of 1, 2 or 3 amino acids) relative to a reference sequence.

Polypeptides of the invention may comprise fragments of SEQ ID NOs 1 to 13. The fragments should comprise at least n consecutive amino acids from the sequences and, depending on the particular sequence, n is 5 or more (e.g. 6, 7 or 8).

Polypeptides of the invention can be prepared in many ways e.g. by chemical synthesis (in whole or in part), by digesting longer polypeptides using proteases, by translation from RNA, by purification from cell culture (e.g. from recombinant expression), etc. A preferred method for production of peptides <40 amino acids long involves in vitro chemical synthesis [7, 8]. Solid-phase peptide synthesis is particularly preferred, such as methods based on tBoc or Fmoc [9] chemistry. Enzymatic synthesis [10] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [11]. Where D-amino acids are included, however, it is preferred to use chemical synthesis. Polypeptides of the invention may have covalent modifications at the C-terminus and/or N-terminus.

Polypeptides of the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides of the invention are preferably provided in purified or substantially purified form i.e. substantially free from other polypeptides (e.g. free from naturally-occurring polypeptides), and are generally at least about 50% pure (by weight), and usually at least about 90% pure i.e. less than about 50%, and more preferably less than about 10% (e.g. 5% or less) of a composition is made up of other expressed polypeptides.

Polypeptides of the invention may be attached to a solid support. Polypeptides of the invention may comprise a detectable label (e.g. a radioactive or fluorescent label, or a biotin label).

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains.

The invention provides polypeptides comprising one or more sequences —X—Y— or —Y—X— or —X—X—, wherein: —X— is an amino acid sequence as defined above and —Y— is not a sequence as defined above i.e. the invention provides fusion proteins. For example, the invention provides —$X_1$—$Y_1$—$X_2$—$Y_2$—, or $X_1$—$X_2$—$Y_1$ or —$X_1$—$X_2$— etc. In one embodiment of the invention, Y is an N-terminal leader sequence as seen for example in SEQ ID No 14 or 15. In a further embodiment, Y is a C-terminal T-helper sequence as seen for example in SEQ ID No 16 or 17.

The invention provides a process for producing polypeptides of the invention, comprising the step of culturing a host cell of to the invention under conditions which induce polypeptide expression.

The invention provides a process for producing a polypeptide of the invention, wherein the polypeptide is synthesised in part or in whole using chemical means.

Drug Design and Peptidomimetics

Polypeptides of the invention are useful in providing immunity against MenB in their own right. However, they may be refined to improve their activity (either general or specific) or to improve pharmacologically important features such as bio-availability, toxicology, metabolism, pharmacokinetics etc. The polypeptides may therefore be used as lead compounds for further research and refinement.

Polypeptides of the invention can be used for designing peptidomimetic molecules [e.g. refs. 12 to 17]. These will typically be isosteric with respect to the polypeptides of the invention but will lack one or more of their peptide bonds. For example, the peptide backbone may be replaced by a non-peptide backbone while retaining important amino acid side chains.

The peptidomimetic molecule may comprise sugar amino acids [18]. Peptoids may be used.

To assist in the design of peptidomimetic molecules, a pharmacophore (i.e. a collection of chemical features and 3D constraints that expresses specific characteristics responsible for activity) can be defined for the peptides. The pharmacophore preferably includes surface-accessible features, more preferably including hydrogen bond donors and acceptors, charged/ionisable groups, and/or hydrophobic patches. These may be weighted depending on their relative importance in conferring activity [19].

Pharmacophores can be determined using software such as CATALYST (including HypoGen or HipHop) [20], $CERIUS^2$, or constructed by hand from a known conformation of a polypeptide of the invention. The pharmacophore can be used to screen structural libraries, using a program such as CATALYST. The CLIX program [21] can also be used, which searches for orientations of candidate molecules in structural databases that yield maximum spatial coincidence with chemical groups which interact with the receptor.

The binding surface or pharmacophore can be used to map favourable interaction positions for functional groups (e.g. protons, hydroxyl groups, amine groups, hydrophobic groups) or small molecule fragments. Compounds can then be designed de novo in which the relevant functional groups are located in substantially the same spatial relationship as in polypeptides of the invention.

Functional groups can be linked in a single compound using either bridging fragments with the correct size and geometry or frameworks which can support the functional groups at favourable orientations, thereby providing a peptidomimetic compound according to the invention. Whilst linking of functional groups in this way can be done manually, perhaps with the help of software such as QUANTA or SYBYL, automated or semi-automated de novo design approaches are also available, such as:

MCSS/HOOK [22, 23, 20], which links multiple functional groups with molecular templates taken from a database.

LUDI [24, 20], which computes the points of interaction that would ideally be fulfilled by a ligand, places fragments in the binding site based on their ability to interact with the receptor, and then connects them to produce a ligand.

MCDLNG [25], which fills a receptor binding site with a close-packed array of generic atoms and uses a Monte Carlo procedure to randomly vary atom types, positions, bonding arrangements and other properties.

GROW [26], which starts with an initial 'seed' fragment (placed manually or automatically) and grows the ligand outwards.

SPROUT [27], suite which includes modules to: identify favourable hydrogen bonding and hydrophobic regions within a binding pocket (HIPPO module); select functional groups and position them at target sites to form starting fragments for structure generation (EleFAnT); generate skeletons that satisfy the steric constraints of the binding pocket by growing spacer fragments onto the start fragments and then connecting the resulting part skeletons (SPIDeR); substitute hetero atoms into the skeletons to generate molecules with the electrostatic properties that are complementary to those of the receptor site (MARABOU). The solutions can be clustered and scored using the ALLigaTOR module.

CAVEAT [28], which designs linking units to constrain acyclic molecules.

LEAPFROG [29], which evaluates ligands by making small stepwise structural changes and rapidly evaluating the binding energy of the new compound. Changes are kept or discarded based on the altered binding energy, and structures evolve to increase the interaction energy with the receptor.

GROUPBUILD [30], which uses a library of common organic templates and a complete empirical force field description of the non-bonding interactions between a ligand and receptor to construct ligands that have chemically reasonable structure and have steric and electrostatic properties complimentary to the receptor binding site.

RASSE [31]

These methods identify relevant compounds. These compounds may be designed de novo, may be known compounds, or may be based on known compounds. The compounds may be useful themselves, or they may be prototypes which can be used for further pharmaceutical refinement (i.e. lead compounds) in order to improve binding affinity or other pharmacologically important features (e.g. bio-availability, toxicology, metabolism, pharmacokinetics etc.).

As well as being useful compounds individually, ligands identified in silico by the structure-based design techniques can also be used to suggest libraries of compounds for 'traditional' in vitro or in vivo screening methods. Important pharmaceutical motifs in the ligands can be identified and mimicked in compound libraries (e.g. combinatorial libraries) for screening for relevant activity.

Nucleic Acids

The invention also provides nucleic acid encoding the polypeptides of the invention. The nucleic acid of the invention may comprise nucleotide sequence selected from SEQ ID Nos 18-32.

The invention also provides nucleic acid comprising nucleotide sequences having sequence identity to such nucleotide sequences. Identity between sequences is preferably determined by the Smith-Waterman homology search algorithm as described above. Depending on the particular sequence, the degree of sequence identity is preferably greater than 50% (e.g. 60%, 70%, 75%, 80%, 85%, 90%, 91%, 92%, 93%, 94%, 95%, 96%, 97%, 98%, 99% or more).

The invention provides nucleic acid of formula 5'-X—Y—Z-3', 5'-X—Y-3', 5'-Y—Z-3' wherein: —X— is a nucleotide sequence (SEQ ID Nos 35, 36) encoding a leader sequence of SEQ ID NO. 14 or 15; —Z— is a nucleotide sequence (SEQ ID No. 37, 38) encoding a T-helper sequence of SEQ ID No. 16, 17; and —Y— is a nucleotide sequence selected from SEQ ID NOS: 18-32.

The invention includes nucleic acid comprising sequences complementary to these sequences (e.g. for antisense or probing, or for use as primers).

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably provided in purified or substantially purified form i.e. substantially free from other nucleic acids (e.g. free from naturally-occurring nucleic acids), generally being at least about 50% pure (by weight), and usually at least about 90% pure.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention can be prepared in many ways e.g. by chemical synthesis (at least in part), by digesting longer nucleic acids using nucleases (e.g. restriction enzymes), by joining shorter nucleic acids (e.g. using ligases or polymerases), from genomic or cDNA libraries, etc.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T). The terms also imply a direction—the complement of 5'-ACAGT-3' is 5'-ACTGT-3' rather than 5'-TGTCA-3'.

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

The invention provides vectors comprising nucleotide sequences of the invention (e.g. cloning or expression vectors) and host cells transformed with such vectors.

Nucleic Acid Immunisation

Nucleic acid immunisation is now a developed field (e.g. see references 32 to 39 etc.), and has been applied to *Neisseria meningitidis* vaccines (e.g. reference 40).

The nucleic acid encoding the polypeptide of the invention is expressed in viva after delivery to a patient and the expressed polypeptide then stimulates the immune system. The active ingredient will typically take the form of a nucleic acid vector comprising: (i) a promoter; (ii) a sequence encoding the polypeptide, operably linked to the promoter; and optionally (iii) a selectable marker. Preferred vectors may further comprise (iv) an origin of replication; and (v) a transcription terminator downstream of and operably linked to (ii). In general, (i) & (v) will be eukaryotic and (iii) & (iv) will be prokaryotic.

Preferred promoters are viral promoters e.g. from cytomegalovirus (CMV). The vector may also include transcriptional regulatory sequences (e.g. enhancers) in addition to the promoter and which interact functionally with the promoter. Preferred vectors include the immediate-early CMV enhancer/promoter, and more preferred vectors also include CMV intron A. The promoter is operably linked to a downstream sequence encoding a polypeptide of the invention, such that expression of the polypeptide-encoding sequence is under the promoter's control.

Where a marker is used, it preferably functions in a microbial host (e.g. in a prokaryote, in a bacteria, in a yeast). The marker is preferably a prokaryotic selectable marker (e.g. transcribed under the control of a prokaryotic promoter). For convenience, typical markers are antibiotic resistance genes.

The vector of the invention is preferably an autonomously replicating episomal or extrachromosomal vector, such as a plasmid.

The vector of the invention preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the polypeptide-encoding sequence. The vectors will therefore (a) be amplified and selected in prokaryotic hosts without polypeptide expression, but (b) be expressed in eukaryotic hosts without being amplified. This arrangement is ideal for nucleic acid immunization vectors.

The vector of the invention may comprise a eukaryotic transcriptional terminator sequence downstream of the coding sequence. This can enhance transcription levels. Where the coding sequence does not have its own, the vector of the invention preferably comprises a polyadenylation sequence. A preferred polyadenylation sequence is from bovine growth hormone.

The vector of the invention may comprise a multiple cloning site.

In addition to sequences encoding the polypeptide of the invention and a marker, the vector may comprise a second eukaryotic coding sequence. The vector may also comprise an IRES upstream of said second sequence in order to permit translation of a second eukaryotic polypeptide from the same transcript as the polypeptide of the invention. Alternatively, the sequence encoding the polypeptide of the invention may be downstream of an IRES.

The vector of the invention may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Vectors may be delivered in a targeted way. Receptor-mediated DNA delivery techniques are described in, for example, references 41 to 46. Therapeutic compositions containing a nucleic acid are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally references 47 to 50).

Viral-based vectors for delivery of a desired nucleic acid and expression in a desired cell are well known in the art. Exemplary viral-based vehicles include, but are not limited to, recombinant retroviruses (e.g. references 51 to 61), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see refs. 62 to 67). Administration of DNA linked to killed adenovirus [68] can also be employed.

Non-viral delivery vehicles and methods can also be employed, including, but not limited to, polycationic condensed DNA linked or unlinked to killed adenovirus alone [e.g. 68], ligand-linked DNA [69], eukaryotic cell delivery vehicles cells [e.g. refs. 70 to 74] and nucleic charge neutralization or fusion with cell membranes. Naked DNA can also be employed. Exemplary naked DNA introduction methods are described in refs. 75 and 76. Liposomes (e.g. immunoliposomes) that can act as gene delivery vehicles are described in refs. 77 to 81. Additional approaches are described in references 82 & 83.

Further non-viral delivery suitable for use includes mechanical delivery systems such as the approach described in ref. 83. Moreover, the coding sequence and the product of expression of such can be delivered through deposition of photopolymerized hydrogel materials or use of ionizing radiation [e.g. refs. 84 & 85]. Other conventional methods for gene delivery that can be used for delivery of the coding sequence include, for example, use of hand-held gene transfer particle gun [86] or use of ionizing radiation for activating transferred genes [84 & 87].

Delivery DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

Pharmaceutical Compositions and Uses

The invention provides compositions comprising: (a) polypeptide, peptidomimetic, antibody, and/or nucleic acid of the invention; and (b) a pharmaceutically acceptable carrier. These compositions may be suitable as immunogenic compositions, for instance, or as diagnostic reagents, or as vaccines. Vaccines according to the invention may either be prophylactic (i.e. to prevent infection) or therapeutic (i.e. to treat infection), but will typically be prophylactic Prophylactic use includes situations where contact with menB is expected and where establishment of infection is to be prevented. For instance, the composition may be administered prior to surgery.

Component (a) is the active ingredient in the composition, and this is present at a therapeutically effective amount i.e. an amount sufficient to inhibit bacterial growth and/or survival in a patient, and preferably an amount sufficient to eliminate bacterial infection. The precise effective amount for a given patient will depend upon their size and health, the nature and extent of infection, and the composition or combination of compositions selected for administration. The effective amount can be determined by routine experimentation and is within the judgment of the clinician. For purposes of the present invention, an effective dose will generally be from about 0.01 mg/kg to about 5 mg/kg, or about 0.01 mg/kg to about 50 mg/kg or about 0.05 mg/kg to about 10 mg/kg. Pharmaceutical compositions based on polypeptides and nucleic acids are well known in the art. Polypeptides may be included in the composition in the form of salts and/or esters.

A 'pharmaceutically acceptable carrier' includes any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in ref. 88.

Compositions of the invention may include an antimicrobial, particularly if packaged in a multiple dose format.

Compositions of the invention may comprise detergent e.g. a Tween (polysorbate), such as Tween 80. Detergents are generally present at low levels e.g. <0.01%.

Compositions of the invention may include sodium salts (e.g. sodium chloride) to give tonicity. A concentration of 10±2 mg/ml NaCl is typical.

Compositions of the invention will generally include a buffer. A phosphate buffer is typical.

Compositions of the invention may comprise a sugar alcohol (e.g. mannitol) or a disaccharide (e.g. sucrose or trehalose) e.g. at around 15-30 mg/ml (e.g. 25 mg/ml), particularly if they are to be lyophilised or if they include material which has been reconstituted from lyophilised material. The pH of a composition for lyophilisation may be adjusted to around 6.1 prior to lyophilisation.

Polypeptides of the invention may be administered in conjunction with other immunoregulatory agents. In particular, compositions will usually include a vaccine adjuvant. Adjuvants which may be used in compositions of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 89], or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being preferred. Mineral containing compositions may also be formulated as a particle of metal salt [90].

Aluminum salts may be included in vaccines of the invention such that the dose of $Al^{3+}$ is between 0.2 and 1.0 mg per dose.

A typical aluminium phosphate adjuvant is amorphous aluminium hydroxyphosphate with $PO_4$/Al molar ratio between 0.84 and 0.92, included at 0.6 mg $Al^{3+}$/ml. Adsorption with a low dose of aluminium phosphate may be used e.g. between 50 and 100 μg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants in the invention include squalene-water emulsions, such as MF59 (5% Squalene, 0.5% Tween 80, and 0.5% Span 85, formulated into submicron particles using a microfluidizer) [Chapter 10 of ref. 89; see also refs. 91-93]. MF59 is used as the adjuvant in the FLUAD™ influenza virus trivalent subunit vaccine.

Particularly preferred adjuvants for use in the compositions are submicron oil-in-water emulsions. Preferred submicron oil-in-water emulsions for use herein are squalene/water emulsions, optionally containing varying amounts of MTP-PE, such as a submicron oil-in-water emulsion containing 4-5% w/v squalene, 0.25-1.0% w/v Tween 80 (polyoxyethylenesorbitan monooleate), and/or 0.25-1.0% Span 85 (sorbitan trioleate), and, optionally, N-acetylmuramyl-L-alanyl-D-isoglutaminyl-L-alanine-2-(1'-2'-dipalmitoyl-sn-glycero-3-hydroxyphosphophoryloxy)-ethylamine (MTP-PE). Submicron oil-in-water emulsions, methods of making the same and immunostimulating agents, such as muramyl peptides, for use in the compositions, are described in detail in references 91 & 94-95.

Complete Freund's adjuvant (CFA) and incomplete Freund's adjuvant (IFA) may also be used as adjuvants in the invention.

C. Saponin Formulations [Chapter 22 of Ref. 89]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C.

Preferably, the saponin is QS21. A method of production of QS21 is disclosed in ref. 96. Saponin formulations may also comprise a sterol, such as cholesterol [97].

Combinations of saponins and cholesterols can be used to form unique particles called immunostimulating complexes (ISCOMs) [chapter 23 of ref. 89]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 97-99. Optionally, the ISCOMS may be devoid of additional detergent(s) [100].

A review of the development of saponin based adjuvants can be found in refs. 101 & 102.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 103-108. Virosomes are discussed further in, for example, ref. 109

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 110. Such "small particles" of 3dMPL are small enough to be sterile filtered through a 0.22 μm membrane [110]. Other non-toxic LPS derivatives include monophosphoryl lipid A mimics, such as aminoalkyl glucosaminide phosphate derivatives e.g. RC-529 [111, 112].

Lipid A derivatives include derivatives of lipid A from *Escherichia coli* such as OM-174. OM-174 is described for example in refs. 113 & 114.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 115, 116 and 117 disclose possible analog substitutions e.g. replacement of guanosine with 2'-deoxy-7-deazaguanosine. The adjuvant effect of CpG oligonucleotides is further discussed in refs. 118-123.

The CpG sequence may be directed to TLR9, such as the motif GTCGTT or TTCGTT [124]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 125-127. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 124 & 128-130.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 131 and as parenteral adjuvants in ref. 132. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 133-140. Numerical reference for amino acid substitutions is preferably based on the alignments of the A and B subunits of ADP-ribosylating toxins set forth in ref. 141, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [142], etc.) [143], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [144] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [145].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 89)

Examples of liposome formulations suitable for use as adjuvants are described in refs. 146-148.

J. Polyoxyethylene Ether and Polyoxyethylene Ester Formulations

Adjuvants suitable for use in the invention include polyoxyethylene ethers and polyoxyethylene esters [149]. Such formulations further include polyoxyethylene sorbitan ester surfactants in combination with an octoxynol [150] as well as polyoxyethylene alkyl ethers or ester surfactants in combination with at least one additional non-ionic surfactant such as an octoxynol [151]. Preferred polyoxyethylene ethers are selected from the following group: polyoxyethylene-9-lauryl ether (laureth 9), polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 152 and 153.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-m-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 154 and 155.

N. Thiosemicarbazone Compounds.

Examples of thiosemicarbazone compounds, as well as methods of formulating, manufacturing, and screening for compounds all suitable for use as adjuvants in the invention include those described in ref 156. The thiosemicarbazones are particularly effective in the stimulation of human peripheral blood mononuclear cells for the production of cytokines, such as TNF-$\alpha$.

O. Tryptanthrin Compounds.

Examples of tryptanthrin compounds, as well as methods of formulating, manufacturing, and screening for compounds all suitable for use as adjuvants in the invention include those described in ref. 157. The tryptanthrin compounds are particularly effective in the stimulation of human peripheral blood mononuclear cells for the production of cytokines, such as TNF-$\alpha$.

The invention may also comprise combinations of one or more of the adjuvants identified above. For example, the following combinations may be used as adjuvant compositions in the invention: (1) a saponin and an oil-in-water emulsion [158]; (2) a saponin (e.g. QS21)+a non-toxic LPS derivative (e.g. 3dMPL) [159]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [160]; (5) combinations of 3dMPL with, for example, QS21 and/or oil-in-water emulsions [161]; (6) SAF, containing 10% squalene, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (8) one or more mineral salts (such as an aluminum salt)+a non-toxic derivative of LPS (such as 3dMPL); and (9) one or more mineral salts (such as an aluminum salt)+an immunostimulatory oligonucleotide (such as a nucleotide sequence including a CpG motif).

Other substances that act as immunostimulating agents are disclosed in chapter 7 of ref. 89.

The use of an aluminium hydroxide or aluminium phosphate adjuvant is particularly preferred, and antigens are generally adsorbed to these salts. Calcium phosphate is another preferred adjuvant.

The pH of compositions of the invention is preferably between 6 and 8, preferably about 7. Stable pH may be maintained by the use of a buffer. Where a composition comprises an aluminium hydroxide salt, it is preferred to use a histidine buffer [162]. The composition may be sterile and/or pyrogen-free. Compositions of the invention may be isotonic with respect to humans.

Compositions may be presented in vials, or they may be presented in ready-filled syringes. The syringes may be supplied with or without needles. A syringe will include a single dose of the composition, whereas a vial may include a single dose or multiple doses. Injectable compositions will usually be liquid solutions or suspensions. Alternatively, they may be presented in solid form (e.g. freeze-dried) for solution or suspension in liquid vehicles prior to injection.

Compositions of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Where a composition of the invention is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed, By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials, and a typical quantity of each meningococcal saccharide antigen per dose is between 1 µg and 10 mg per antigen.

The patient is preferably a human. The human may be an adult or a child.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, sublingual, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. The nucleic acid of the present invention may be used as a primer followed by a polypeptide of the present invention as a booster. Suitable timing between priming doses (e.g. between 4-16 weeks), and between priming and boosting, can be routinely determined.

Further Antigenic Components of Compositions of the Invention

The invention also provides a composition comprising a polypeptide of the invention and one or more of the following further antigens:
- a saccharide antigen from *N. meningitidis* serogroup A, C, W135 and/or Y (preferably all four), such as the oligosaccharide disclosed in ref. 163 from serogroup C [see also ref. 164] or the oligosaccharides of ref. 165.
- a saccharide antigen from *Streptococcus pneumoniae* [e.g. 166, 167, 168].
- an antigen from hepatitis A virus, such as inactivated virus [e.g. 169, 170].
- an antigen from hepatitis B virus, such as the surface and/or core antigens [e.g. 170, 171].
- a diphtheria antigen, such as a diphtheria toxoid [e.g. chapter 3 of ref. 172] e.g. the $CRM_{197}$ mutant [e.g. 173].
- a tetanus antigen, such as a tetanus toxoid [e.g. chapter 4 of ref. 172].
- an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 174 & 175].
- a saccharide antigen from *Haemophilus influenzae* B [e.g. 164].
- polio antigen(s) [e.g. 176, 177] such as IPV.
- measles, mumps and/or rubella antigens [e.g. chapters 9, 10 & 11 of ref. 172].
- influenza antigen(s) [e.g. chapter 19 of ref. 172], such as the haemagglutinin and/or neuraminidase surface proteins.
- an antigen from *Moraxella catarrhalis* [e.g. 178].
- a saccharide antigen from *Streptococcus agalactiae* (group B *streptococcus*).
- an protein antigen from *Streptococcus agalactiae* (group B *streptococcus*) [e.g. 179, 180].
- an antigen from *Streptococcus pyogenes* (group A *streptococcus*) [e.g. 180, 181, 182].
- an antigen from *Staphylococcus aureus* [e.g. 183].

Toxic protein antigens may be detoxified where necessary (e.g. detoxification of pertussis toxin by chemical and/or genetic means [175]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include bacterial toxins (such as diphtheria toxoid or tetanus toxoid), the *N. meningitidis* outer membrane protein [184], synthetic peptides [185, 186], heat shock proteins [187, 188], pertussis proteins [189, 190], protein D from *H. influenzae* [191, 192], cytokines [193], lymphokines [193], *H. influenzae* proteins, hormones [193], growth factors [193], toxin A or B from *C. difficile* [194], iron-uptake proteins [195], artificial proteins comprising multiple human CD4+ T cell epitopes from various pathogen-derived antigens [196] such as the N19 protein [197], pneumococcal surface protein PspA [198], pneumolysin [199], etc. A preferred carrier protein is CRM197 protein [200].

Antigens in the composition will typically be present at a concentration of at least 1 μm/ml each. In general, the concentration of any given antigen will be sufficient to elicit an immune response against that antigen.

As an alternative to using proteins antigens in the immunogenic compositions of the invention, nucleic acid (preferably DNA e.g. in the form of a plasmid) encoding the antigen may be used.

Antigens are preferably adsorbed to an aluminium salt.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

As indicated in the above text, nucleic acids and polypeptides of the invention may include sequences that:
(a) are identical (i.e. 100% identical) to the sequences disclosed in the sequence listing;
(b) share sequence identity with the sequences disclosed in the sequence listing;
(c) have 1, 2, 3, 4, 5, 6, 7, 8, 9 or 10 single nucleotide or amino acid alterations (deletions, insertions, substitutions), which may be at separate locations or may be contiguous, as compared to the sequences of (a) or (b); and
(d) when aligned with a particular sequence from the sequence listing using a pairwise alignment algorithm, a moving window of x monomers (amino acids or nucleotides) moving from start (N-terminus or 5') to end (C-terminus or 3'), such that for an alignment that extends to p monomers (where p>x) there are p−x+1 such windows, each window has at least x·y identical aligned monomers, where: x is selected from 5, 6, 7, 8, 9, 10, 11, 12, 13, 14, 15, 16, 17, 18, 19, 20, 21, 22, 23, 24, 25, 26, 27, 28, 29, 30, y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [201], using default parameters (e.g. with Gap opening penalty=10.0, and with Gap extension penalty=0.5, using the EBLOSUM62 scoring matrix). This algorithm is conveniently implemented in the needle tool in the EMBOSS package [202].

The nucleic acids and polypeptides of the invention may additionally have further sequences to the N-terminus/5' and/or C-terminus/3' of these sequences (a) to (d).

The practice of the present invention will employ, unless otherwise indicated, conventional methods of chemistry, biochemistry, molecular biology, immunology and pharmacology, within the skill of the art. Such techniques are explained fully in the literature. See, e.g., references 203-210, etc.

It will be understood that the invention has been described by way of example only and modifications may be made whilst remaining within the scope and spirit of the invention.

BRIEF DESCRIPTION OF THE SEQUENCE LISTING

| | |
|---|---|
| SEQ ID NO 1 (7M) | PPWDFDAGEGIH |
| SEQ ID NO 2 (8M) | DYAWDDFYAMGD |
| SEQ ID NO 3 (9M) | DYAWDQTHQ |

| | | |
|---|---|---|
| SEQ ID NO 4 (11M) | DYAWDQTHQ | |
| SEQ ID NO 5 (12M) | DYAWDQTHQ | |
| SEQ ID NO 6 (13M) | DAGDSGYLT | |
| SEQ ID NO 7 (15M) | EFDAGDVLL | |
| SEQ ID NO 8 (17M) | DAGDHSHPQ | |
| SEQ ID NO 9 (18M) | DAGEVYPGP | |
| SEQ ID NO 10 (19M) | DAGDSAYSQ | |
| SEQ ID NO 11 (20M) | DAGEGGPRV | |
| SEQ ID NO 12 (21M) | DAGEGGPRV | |
| SEQ ID NO 13 (22M) | DAGDHRAAA | |
| SEQ ID NO: 14 (leader sequence) | MRYMILGLLALAAVCSAAEF | |
| SEQ ID NO 15 (leader sequence) | MRYMILGLLALAAVCSAA | |
| SEQ ID NO 16 (T-helper sequence) | MKLQYIKANSKFIGITELEF | |
| SEQ ID NO 17 (T-helper sequence) | QYIKANSKFIGITELEF | |
| SEQ ID NO 18 (7M) | CCGCCGTGCGACTTCGACGCGGGTGAAGGTATCCAC | |
| SEQ ID NO 19 (7Mp) | CCACCTTGGGATTTCGATGCCGGCGAGGGCATTCAC | |
| SEQ ID NO 20 (8M) | GACTACGCGTGGGACGACTTCTACGCGATGGGGGAT | |
| SEQ ID NO 21 (8Mp) | GATTATGCATGGGATGACTTCTACGCTATGGGTGAC | |
| SEQ ID NO 22 (9M) | GATTACGCATGGGACCAAACCCATTAG | |
| SEQ ID NO 23 (9Mp) | GATTATGCCTGGGATCAGACTCACCAG | |
| SEQ ID NO 24 (13M) | GATGCTGGCGACTCTGGCTATTTTGACG | |
| SEQ ID NO 25 (13Mp) | GATGCCGGCGATTCTGGCTATCTGACT | |
| SEQ ID NO 26 (15M) | GAGTTCGATGCGGGTGACGTGTTGCTG | |
| SEQ ID NO 27 (17M) | GACGCTGGGGACCATTCGCATCCGCAG | |
| SEQ ID NO 28 (17Mp) | GATGCCGGCGATCACTCTCACCCACAG | |
| SEQ ID NO 29 (18M) | GATGCTGGGGAAGTATATCCAGGTCCG | |
| SEQ ID NO 30 (19M) | GACGCCGGCGATTCGGCGTACTCCCAG | |
| SEQ ID NO 31 (20M) | GATGCGGGCGAGGGCGGGCCACGCGTG | |
| SEQ ID NO 32 (22M) | GACGCAGGCGATCATCGCGCGGCGGCG | |
| SEQ ID NO 33 (pS.9M) | DYAWDQTHQDPAK | |
| SEQ ID NO 34 (pS.7M) | PPWDFDAGEGIHGDPAK | |
| SEQ ID NO: 35 (leader sequence) | ATGAGGTACATGATTTTAGGCTTGCTCGCCCTTGCG GCAGTCTGCAGCGCTGCCGAATTC | |
| SEQ ID NO 36 (leader sequence) | ATGAGGTACATGATTTTAGGCTTGCTCGCCCTTGCG GCAGTCTGCAGCGCTGCC | |
| SEQ ID NO 37 (T-helper sequence) | ATGAAACTACAGTATATAAAAGCAAATTCTAAATTT ATAGGTATAACTGAACTAGAATTC | |
| SEQ ID NO 38 (T-helper sequence) | CAGTATATAAAAGCAAATTCTAAATTTATAGGTATA ACTGAACTAGAATTC | |

Wherein 7MP, 8MP, 9MP, 13MP and 17MP represent the plasmid sequences related to the corresponding clone sequences, which were optimized for murine codon preferences.

MODES FOR CARRYING OUT THE INVENTION

Peptide Selection

Figure 1:
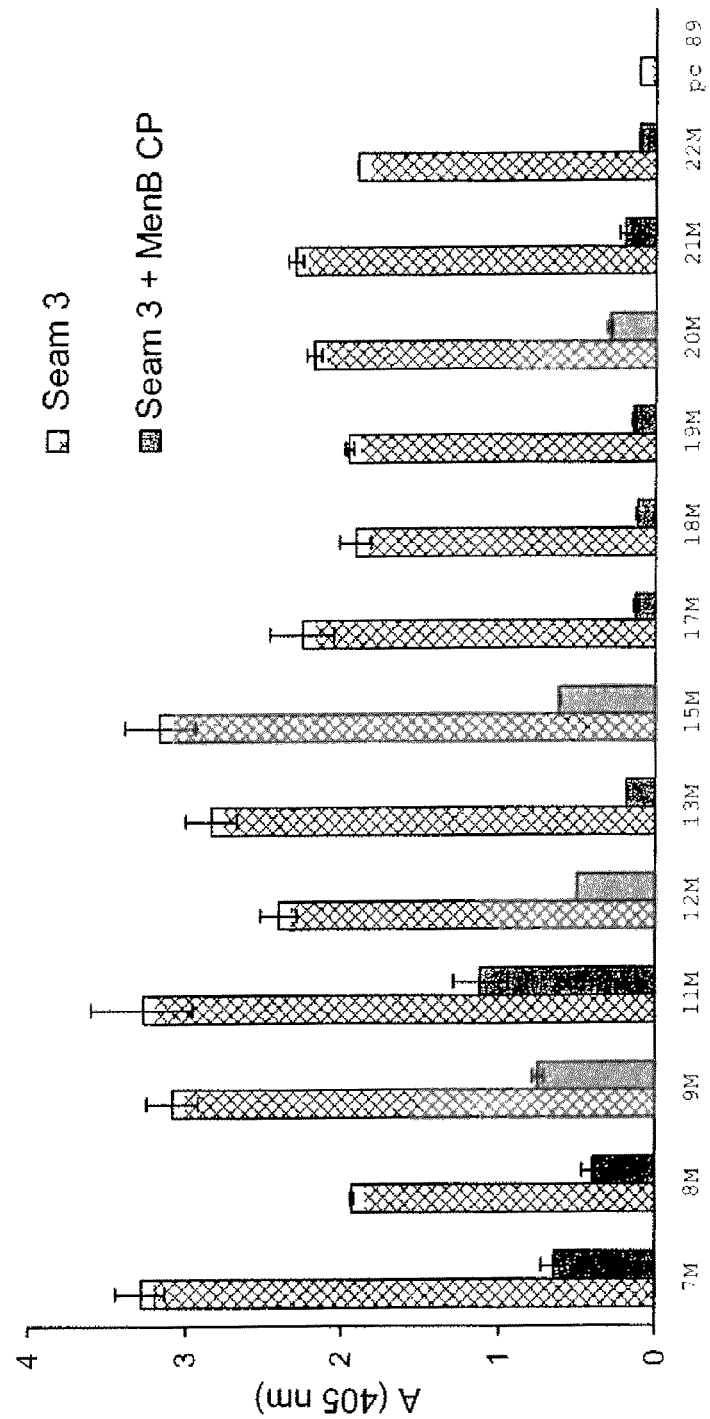
FIG. 1 shows the binding of phage clones to Seam 3. Plates were sensitized with a MAb directed against the gp3 (1 μg/ml) and 100 μl of purified phage clones (10$^{11}$ pfu/ml) were added. After a 2 h incubation the Seam 3 MAb (5 μg/ml) was added in the presence (grey columns) or in the absence (patterned columns) of MenB CP (1 μg/ml). Binding was detected using AP-conjugated anti-mouse IgG Data represents the means±SD of three determinations.

To obtain peptides mimicking a protective, non-human cross-reactive epitope of the Neisseria meningitidis group B capsular polysaccharide (MenB CP), a monoclonal antibody (MAb), Seam 3, recognizing such an epitope, was used as a template. Two combinatorial phage display peptide libraries, based respectively on nonapeptides and dodecapeptides fused to a major coat protein (pVIII) of the M13 phage, were independently used. After three rounds of selection using Seam 3 as bait, 13 phage clones were obtained, two from the dodecapeptide library and eleven from the nonapeptide library, which strongly reacted against Seam 3 (FIG. 1), but not against an isotype-matched irrelevant MAb (not shown). Moreover, binding of all clones was inhibited by purified MenB CP (FIG. 1). This data suggests that the peptides mimic a capsular epitope recognized by the Seam 3 MAb.

PCR-amplified fragments containing the phage inserts were sequenced (Table 1). Of the 13 phage clones obtained, two (20M and 21M) were found to express the sequence DAGEGGPRV, three (9M, 11M and 12M) the sequence DYAWDQTHQD, while the others expressed different sequences with the DAGE/D consensus motif. The less represented consensus sequence DYAWD was noticeable for the presence of tryptophan (W), which is relatively rare in the library inserts. Two clones, 7M and 9M, representative of the two consensus sequences were selected for further studies.

TABLE 1

| CLONE NAME | AMINO ACID SEQUENCE | | | | | | | | | | | | | | |
|---|---|---|---|---|---|---|---|---|---|---|---|---|---|---|---|
| 7M (SEQ ID No 1)  | P | P | W | D | F | D | A | G | E | G | I | H | — | — | — |
| 8M (SEQ ID No 2)  | — | — | — | — | D | Y | A | W | D | D | F | Y | A | M | G | D |
| 9M (SEQ ID No 3)  | — | — | — | — | D | Y | A | W | D | Q | T | H | Q | — | — | — |
| 11M (SEQ ID No 4) | — | — | — | — | D | Y | A | W | D | Q | T | H | Q | — | — | — |
| 12M (SEQ ID No 5) | — | — | — | — | D | Y | A | W | D | Q | T | H | Q | — | — | — |
| 13M (SEQ ID No 6) | — | — | — | — | — | D | A | G | D | S | G | Y | L | T | — | — |
| 15M (SEQ ID No 7) | — | — | — | E | F | D | A | G | D | V | L | L | — | — | — | — |
| 17M (SEQ ID No 8) | — | — | — | — | — | D | A | G | D | H | S | H | P | Q | — | — |
| 18M (SEQ ID No 9) | — | — | — | — | — | D | A | G | E | V | Y | P | G | P | — | — |
| 19M (SEQ ID No 10)| — | — | — | — | — | D | A | G | D | S | A | Y | S | Q | — | — |
| 20M (SEQ ID No 11)| — | — | — | — | — | D | A | G | E | G | G | P | R | V | — | — |
| 21M (SEQ ID No 12)| — | — | — | — | — | D | A | G | E | G | G | P | R | V | — | — |
| 22M (SEQ ID No 13)| — | — | — | — | — | D | A | G | D | H | R | A | A | A | — | — |

Construction of DNA Plasmids and Expression Analysis.

Oligodeoxynucleotides encoding 7M and 9M peptides were cloned in a mammalian vector suitable for DNA vaccination to produce p9M and p7M. A secretory leader sequence from adenovirus E3 or a T helper sequence from tetanus toxoid or both were included in some DNA constructs to increase exogenous expression and provide T cell help, respectively. The resulting plasmids are shown in Table 2.

TABLE 2

| Description | Leader Sequence | T-helper sequence | Antigenic sequence |
|---|---|---|---|
| pCI-neo | — | — | — |
| pS.9M | MRYMILGLLALAAVCSAAEF (SEQ ID No 14) | — | DYAWDQTHQDPAK (SEQ ID No 33) |
| pT.9M | — | MKLQYIKANSKFIGITELEF (SEQ ID No 16) | DYAWDQTHQDPAK (SEQ ID No 33) |
| pST.9M | MRYMILGLLALAAVCSAA (SEQ ID No 15) | QYIKANSKFIGITELEF (SEQ ID No 17) | DYAWDQTHQDPAK (SEQ ID No 33) |
| p9M | — | — | DYAWDQTHQDPAK (SEQ ID No 33) |
| pS.7M | MRYMILGLLALAAVCSAAEF (SEQ ID No 14) | — | DYAWDQTHQDPAK (SEQ ID No 33) |
| pT.7M | — | MKLQYIKANSKFIGITELEF (SEQ ID No 16) | PPWDFDAGEGIHGDPAK (SEQ ID No 34) |
| pST.7M | MRYMILGLLALAAVCSAA (SEQ ID No 15) | QYIKANSKFIGITELEF (SEQ ID No 17) | PPWDFDAGEGIHGDPAK (SEQ ID No 34) |

TABLE 2-continued

| Description | Leader Sequence | T-helper sequence | Antigenic sequence |
|---|---|---|---|
| p7M | — | — | PPWDFDAGEGIHGDPAK (SEQ ID No 34) |
| pmIL12 | — | — | — |
| PmIFN | — | — | — |

Figure 2:
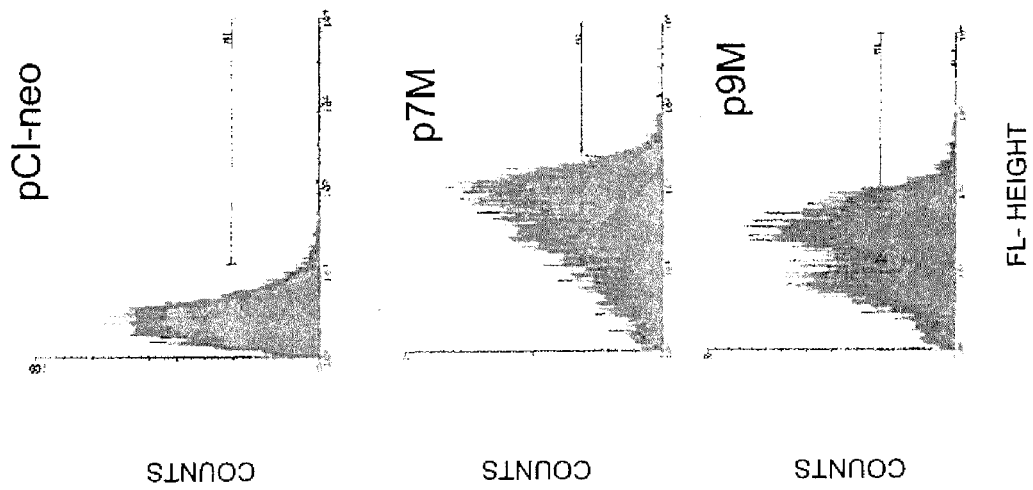
FIG. 2 shows flow cytometric analysis. Binding of the Seam 3 MAb to permeabilized COS-7 cells transfected with expression plasmids containing the p7M or the p9M minigenes is shown. Cells transfected with the empty vector (pCI-neo) were used as controls. After being transiently transfected, cells were permeabilized with Tween 20 and exposed to the Seam 3 MAb (4 μg/ml in PBS). FITC-conjugated anti-mouse IgG was used to detect binding.

The p9M and p7M plasmids were used to transiently transfect COS-7 cells. Protein expression was analyzed by the ability of permeabilized cells to bind the Seam 3 MAb using immunofluorescence. Cells transfected with plasmids showed increased fluorescence relative to cells transfected with the empty plasmid (pCI-neo) after treatment with the Seam 3 MAb followed by FICT-conjugated anti-mouse IgG (FIG. 2). These data indicate that transfection with either p7M or p9M results in expression of the peptides in a functional form, as defined by their ability to bind to the Seam 3 idiotype. Similar data were obtained using the other plasmids listed in Table 2.

Bactericidal Activity after DNA Immunization

Figure 3:
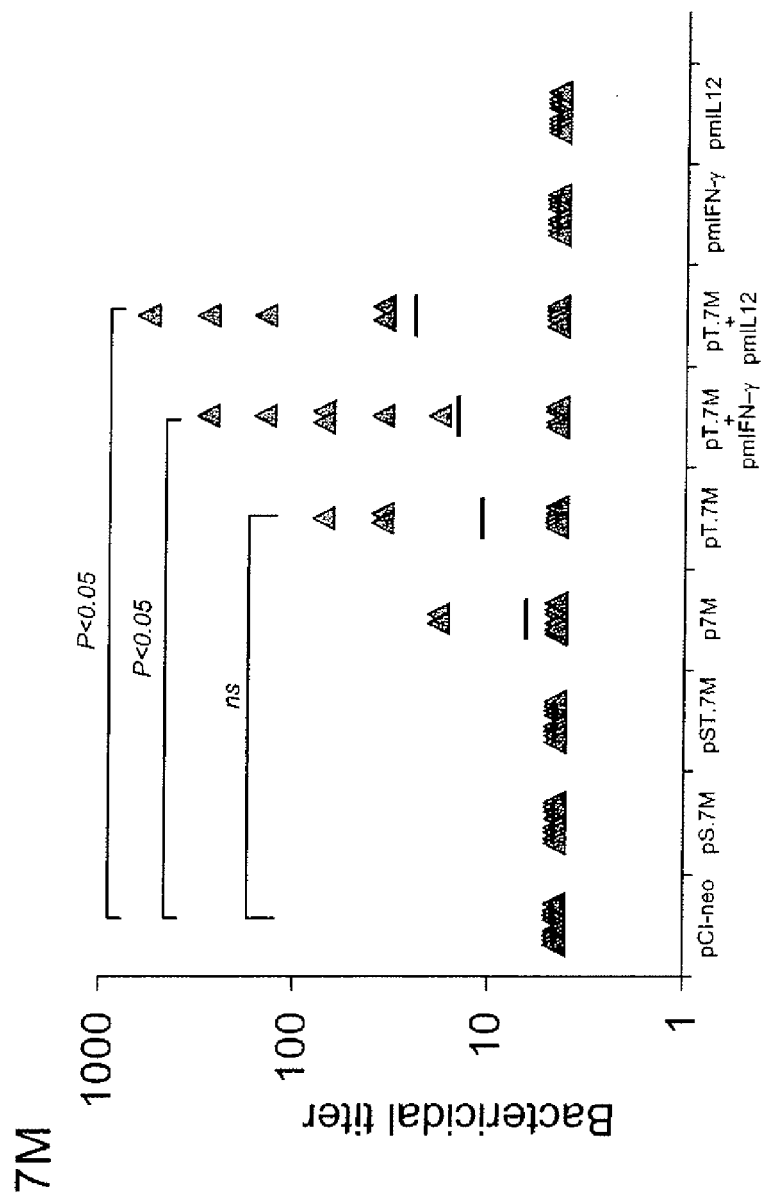
FIG. 3 shows serum bactericidal activity after immunization with the 7M mini-gene. Bactericidal activity in sera from mice immunized with different plasmids containing the 7M sequence or with an empty vector (pCI-neo) was assessed. Plasmids (150 μg) were given i.m three times and serum was collected at day 56 after the first immunization. To calculate mean geometric titers (horizontal bars), sera without detectable bactericidal activity were given an arbitrary titer of 4.5 (i.e. half of the reciprocal of the lowest dilution tested). For a description of the different plasmids see Table Two. P<0.05=significantly different by ANOVA and Student-Newman-Keels test; ns=non significant

Sera from mice immunized i.m. three times, at 21 day-intervals, with the different plasmids (150 µg in 50 µl of PBS) were collected at 56 days after the first immunization and assayed for their ability to induce complement-dependent bactericidal activity. FIG. 3 shows the results obtained after immunization with plasmids containing the 7M gene. Serum bactericidal activity was below the limits of detection of the assay in animals administered the empty vector (pCI-neo, FIG. 3) or in preimmune serum samples (data not shown). There was no detectable bactericidal activity in the sera of animals immunized with the two plasmids containing a secretory signal peptide before the 7M sequence (pS.7M and pST.7M, respectively with or without the T helper epitope). However, 2 and 3 out of 8 animals immunized with the respective plasmids devoid of the signal peptide (p7M and pT.7M) had moderate serum bactericidal activity. Co-administration of pT7.M with plasmids containing the IL-12 or the IFN-γ gene further increased the number of responding animals. In contrast, bactericidal activity was below the detection limit of the assay in animals administered pmIL12 or pmIFN-γ alone. These data indicated that immunization with the 7M mini-gene fused to a T cell epitope sequence produced significant increases in serum bactericidal activity when co-administered with vectors expressing IL-12 or IFN-γ.

Figure 4:
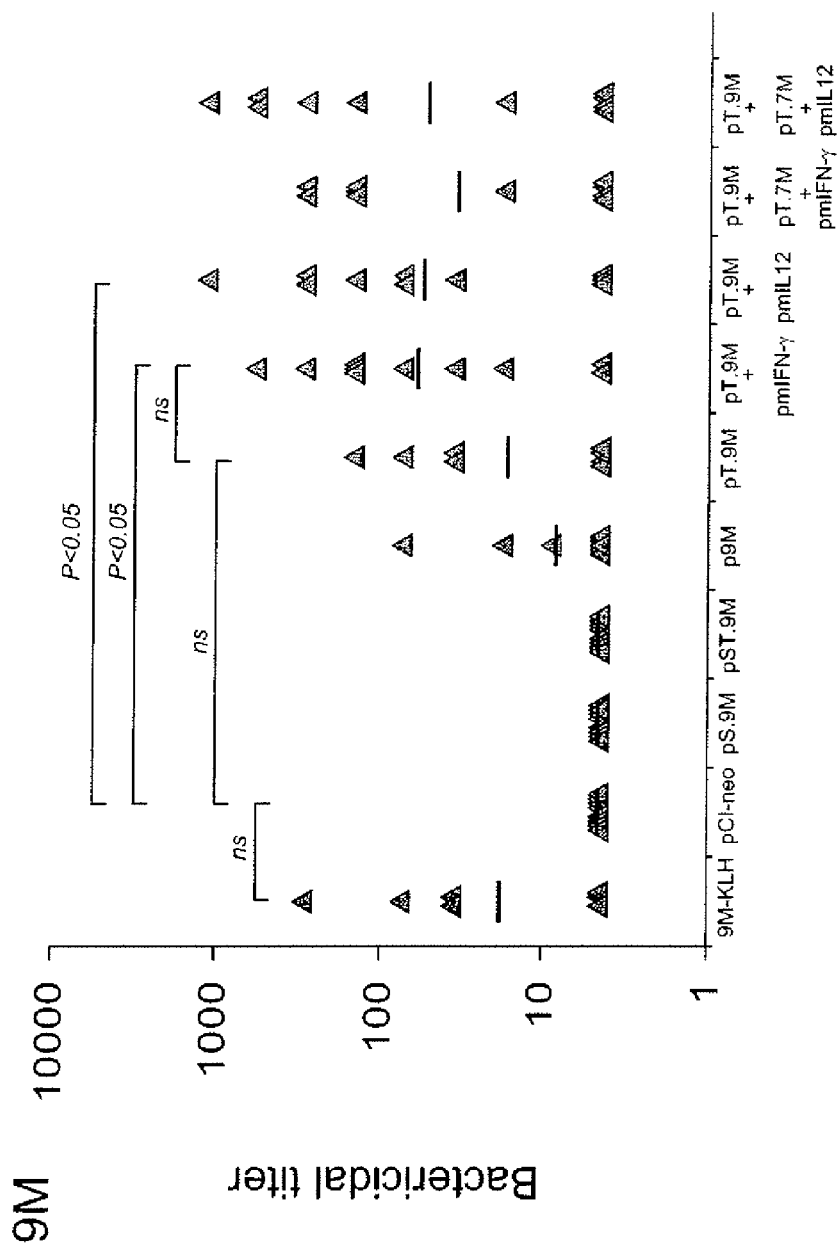
FIG. 4 shows serum bactericidal activity induced by 9M immunization. Bactericidal activity in sera from mice immunized with different plasmids containing the 9M sequence or with an empty vector (pCI-neo) was assessed. Plasmids (150 μg) were given i.m three times and serum was collected at day 56 after the first immunization. For comparison, a group of animals was immunized three times i.p. with the 9M peptide conjugated to KLH (9M-KLH, 100 μg) using Freund's adjuvant. In some experiments mice were co-administered 70 μg of plasmids containing the 7M (pT.7M), the IFN-γ (pmIFN) or the IL-12 (pmIL12) sequences, or the indicated combinations, in addition to the pT.9M plasmid (70 μg). To calculate mean geometric titers (horizontal bars), sera without detectable bactericidal activity were given an arbitrary titer of 4.5 (i.e. half of the reciprocal of the lowest dilution tested). For a description of the different plasmids see Table Two. P<0.05=significantly different by ANOVA and Student-Newman-Keels test; ns=non significant

FIG. 4 shows that similar data were obtained after immunization with plasmids containing the 9M mini-gene. Results were compared with those obtained after immunization in Freund's adjuvant with the 9M peptide conjugated to KLH. Such immunization induced bactericidal activity in half of the animals. Similarly, 3 out of 8 p9M-immunized animals showed detectable serum bactericidal activity. The presence of a T helper epitope in pT.9M tended to further improve mean titers and the percentage of responding animals. Co-administration of pT9M with plasmids containing either the IL-12 or IFN-γ gene increased the number of responding animals to 6/10 and 7/10, respectively. Overall, mean bactericidal titers tended to be higher in 9M-relative to 7M-immunized animals (compare FIGS. 3 and 4). Again, no elevation in serum bactericidal activity was detected in animals immunized with vectors containing a secretory signal sequence (i.e. pS.9M and pST.9M, FIG. 4).

Figure 5:
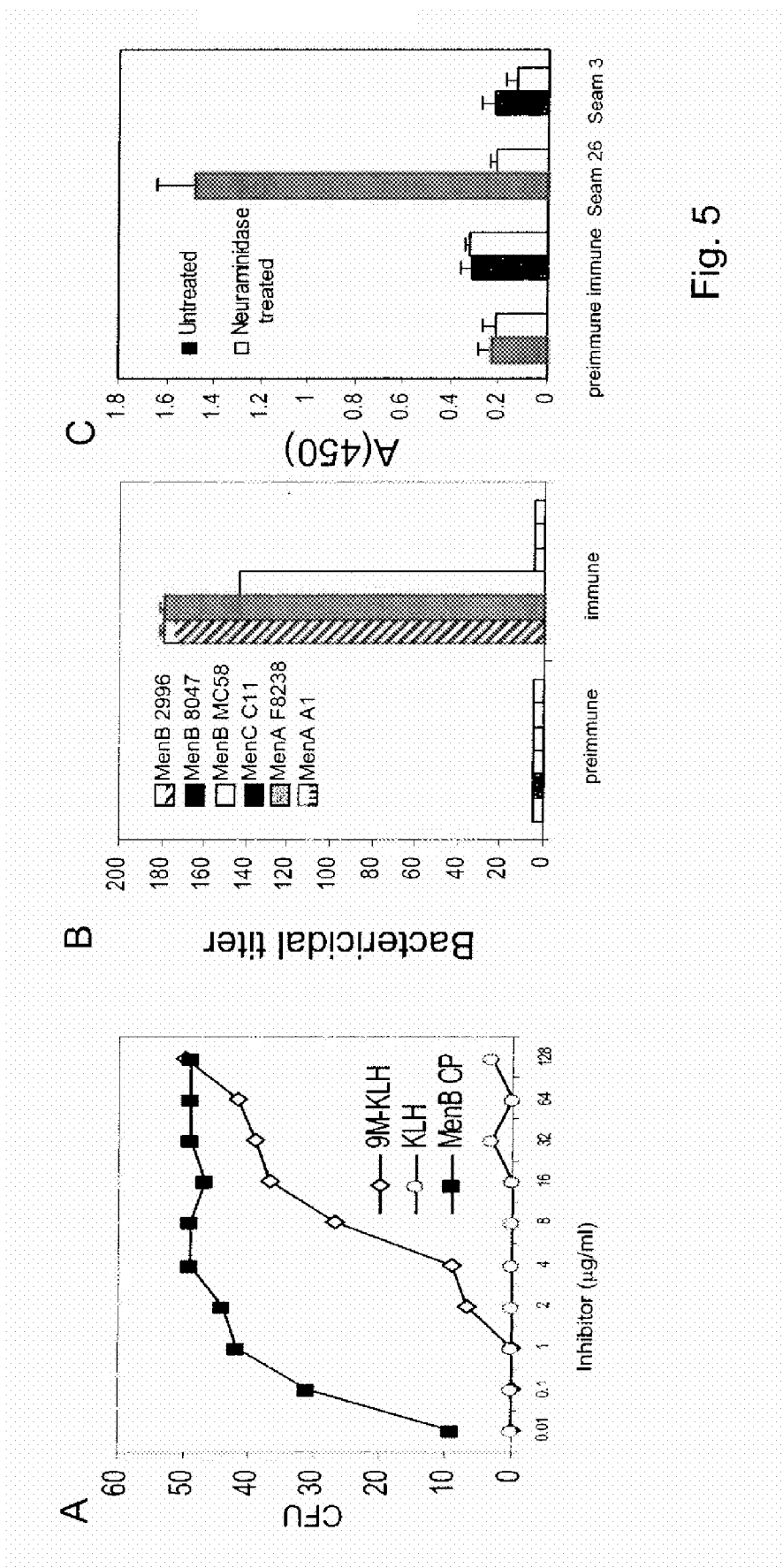
FIG. 5 shows that immunization with the 9M plasmid induces capsule-specific antibodies. The left panel shows inhibition of bactericidal activity by purified N-propionylated MenB CP or 9M-KLH conjugates. KLH served as a control. Serum from a pT.9M+pmIFN-γ-immunized animal was mixed with the inhibitors and tested at a final dilution of 1:100. The vertical axis shows bacterial numbers after completion of the bactericidal assay. Shown is a representative experiment of three, each conducted on a different serum sample obtained from pT.9M+pmIFN-γ(gamma)-immunized animals. The samples were selected from the experiment shown in FIG. 4. The centre panel shows bactericidal activity against different meningococcal strains using the above-mentioned sera from pT.9M+pmIFN-γ (gamma).-immunized animals. Columns and bars represent means±SD. The right panel shows reactivity against human polysialic acid using the same three serum samples from pT.9M+pmIFN-γ (gamma).-immunized animals. Neuraminidase-treated or untreated cells from the polysialic acid-rich CHP 212 human neuroblastoma cell line were fixed in the wells of microtiter plates. Sera were diluted 1:20 and tested for binding to cell-coated plates by ELISA. Seam 3 and Seam 26 monoclonal antibodies were used, respectively, as negative and positive controls at a concentration of 5 micrograms per milliliter. Antibody binding was detected using a polyvalent anti-mouse IgG serum conjugated with alkaline phosphatase. Data represent means+standard deviations of 3 determinations, each conducted on a different serum sample.

Next, it was sought to confirm that the antibody response induced by immunization with the constructs described above was directed against their intended target e.g. the MenB CP. This was considered important since administration with cytokines can produce polyclonal activation. In a representative experiment the bactericidal activity induced by pT.9M-pmIFN-γ co-immunization was totally inhibited by purified MenB CP or by the 9M-KLH conjugate, but not by KLH alone (FIG. 5 left panel). Similar data were obtained with other randomly selected serum samples from the experiment shown in FIG. 4 (not shown). Moreover, bactericidal activity was observed using two additional MenB strains, but not an encapsulated mutant strain (FIG. 5 right panel). Together, this data indicates that pT.9M immunization can induce bactericidal antibodies specific for 9M peptide that cross-react with the MenB CP.

Passive Immunoprotection

Figure 6:
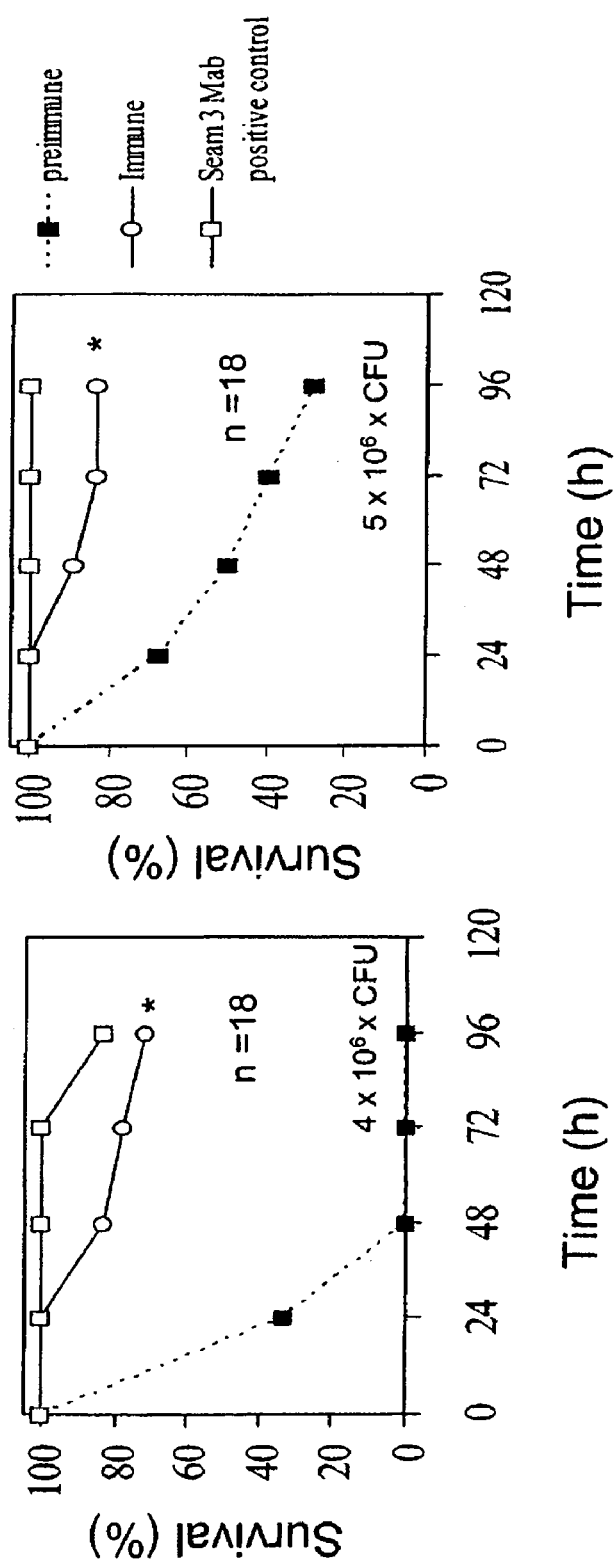
FIG. 6 shows how sera from 9M-immunized animals protect neonatal mice from MenB-induced lethality. The figure shows the lethality of pups (<48 h old) challenged s.c. with the indicated dose of MenB strain 2996. At 4 h before challenge, neonatal mice were administered s.c. 30 μl of a 1/20 dilution of serum from a pT.9M-immunized animal with a bactericidal titer of 1:144. Preimmune serum and the Seam 3 mAb (10 μg in PBS) served as negative and positive controls, respectively. A representative experiment is shown using serum samples from three different animals. *, significantly different from preimmune serum-treated mice by Kaplan-Meier test.

To fully assess the functional properties of antibody responses induced by pT.9M immunization, the ability of immune sera to passively protect neonatal mice from meningococcal infection was studied. In the experiments shown in FIG. 6, the lethality of pups inoculated with a 30 µl of a 1/20 dilution of a serum (with a titer of 144) obtained after pT.9M immunization was observed after challenge with MenB. Pre-immune serum and Seam 3 mAb were included as positive and negative controls, respectively. FIG. 6 shows that mice treated with the immune serum were significantly protected against different bacterial doses. These data indicate that immunization with pT.9M induces serum antibodies with marked protective activity.

Other Species

Figure 7:
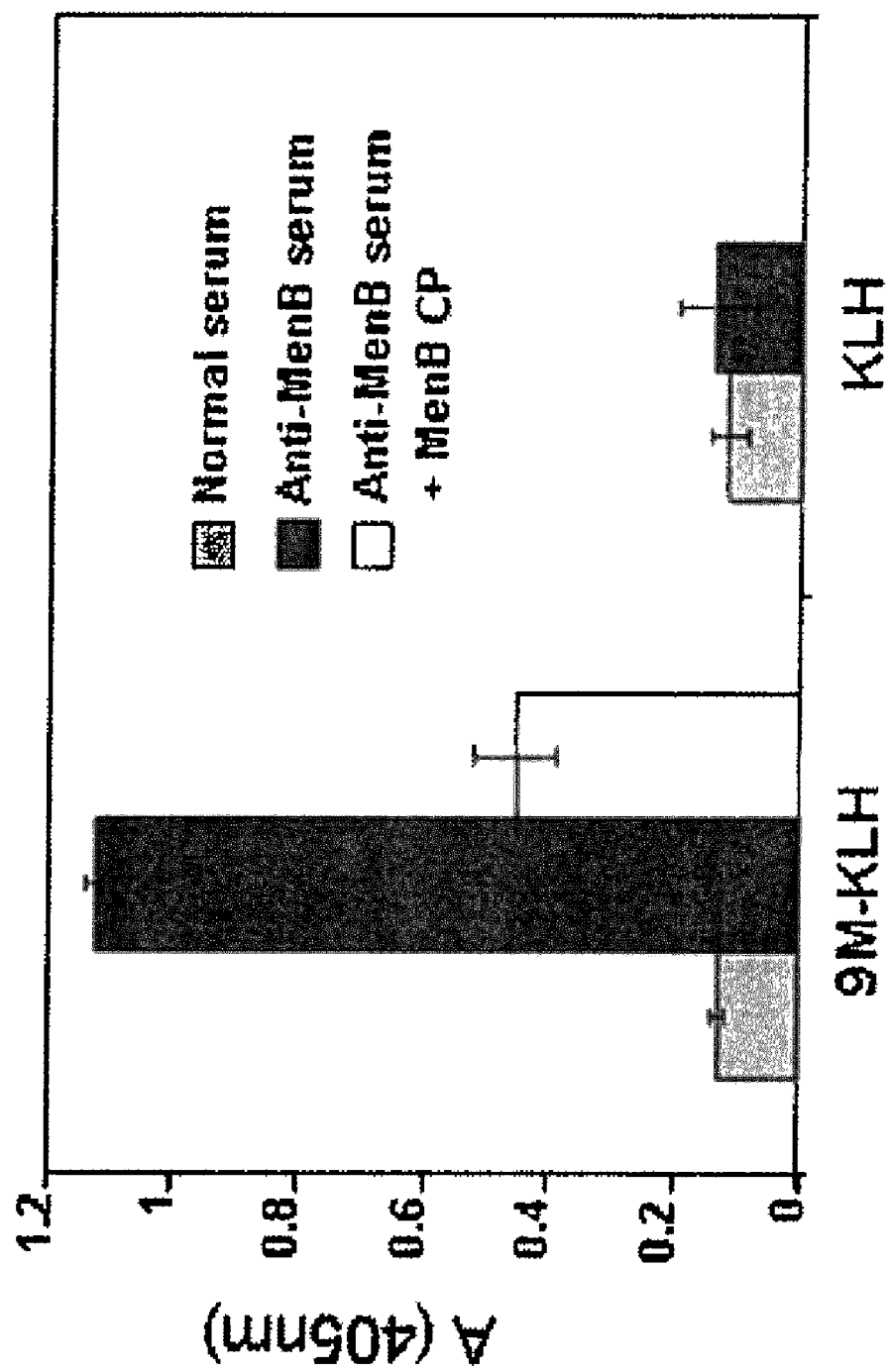
FIG. 7 shows the reactivity of rabbit anti-MenB serum against the 9M peptide mimic. A rabbit serum raised against MenB or normal rabbit serum (both diluted 1:1,000 in PBS) were added to wells sensitized with the 9M-KLH conjugate (5 μg/ml) or with KLH. Anti-MenB serum was used with or without pre-treatment (1 h at 37° C.) with 1 μg/ml of purified MenB CP. Antibody binding was detected by the addition of biotin-conjugated goat anti-rabbit IgG (diluted 1:10,000) followed by streptavidin-alkaline phosphate and p-nitrophenylphosphate.

In additional experiments it was investigated whether anti-MenB CP antibodies from species other than mouse could recognize the 9M mimic. Isotype distribution of anti-9M antibodies was determined by ELISA, using 9M-KLH (7 µg/ml) as coating antigen. Serum samples were diluted 1:100 in PBS supplemented with 10 µg/ml of KLH before addition to the wells. Anti-human PSA antibodies were detected by using untreated or neuraminidase-treated neuroblastoma CHP 212 cells, expressing high levels of PSA. Anti-MenB CP antibody titers were determined by ELISA. FIG. 7 shows that anti-MenB CP antibodies from species other than mouse could indeed recognize the 9M mimic. In the ELISA assay a polyclonal anti-MenB rabbit serum, but not normal serum, reacted against the 9M-KLH conjugate. Moreover, in this assay, binding was inhibited by the addition of purified Men-B CP (FIG. 7). These data indicate that the 9M peptide mimotope specifically interacts not only with the mAb used for its selection, but also with polyclonal MenB CP-specific rabbit antibodies.

Effects of DNA-Priming Followed by Peptide-Boosting

Figure 8:
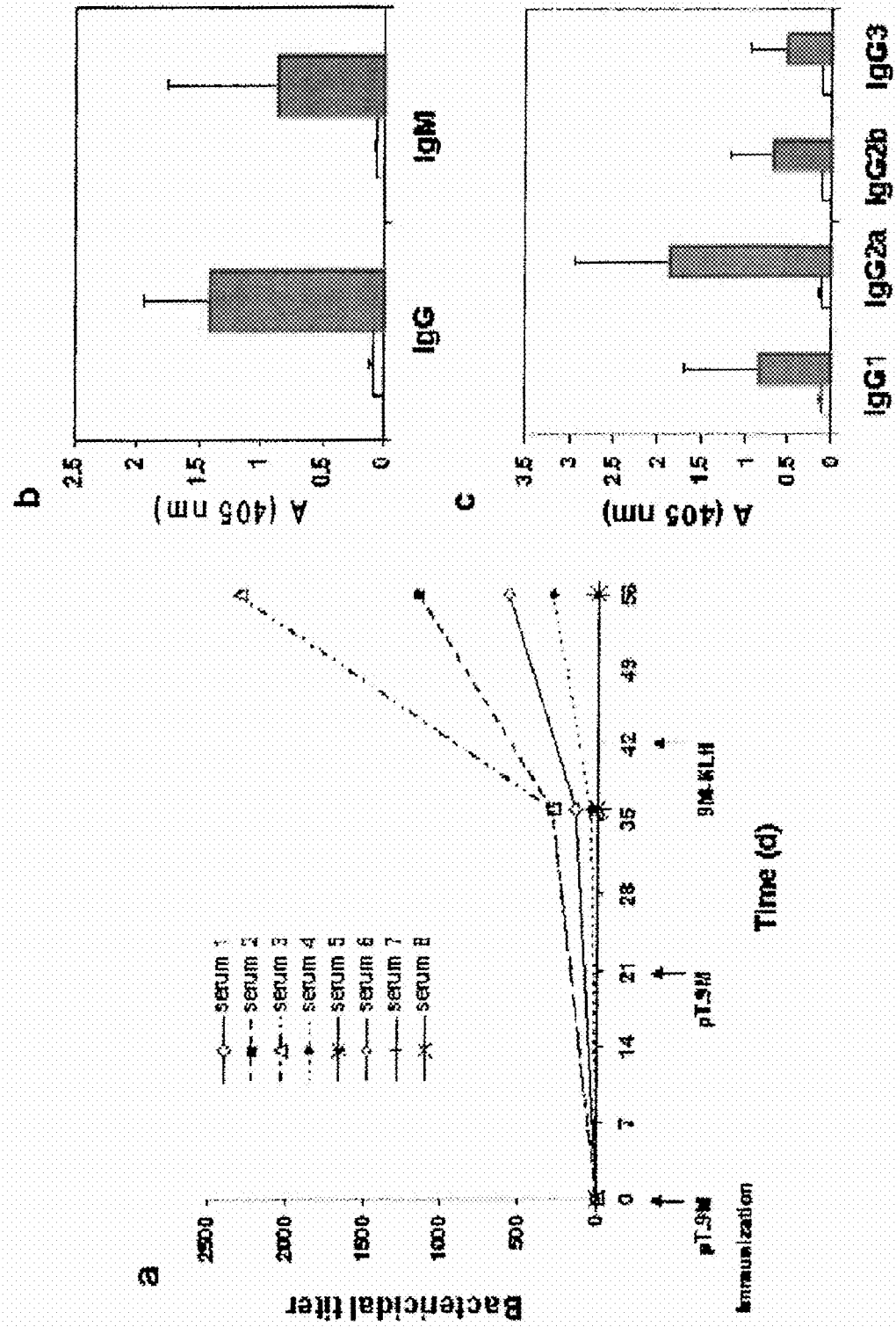
FIG. 8 shows that prime-boosting increases serum bactericidal activity and induces a Th1 response. The left panel shows serum bactericidal activity in animals primed with pT.9M on day 0 and 21 and boosted with the 9M peptide conjugated with KLH (9M-KLH) at day 42. The top and bottom right panel show the isotype distribution of anti-9M antibodies in sera from prime-boosted animals. Plates were sensitized with 9M-KLH (7 μg/ml) before the addition of sera diluted 1:100 in PBS supplemented with KLH (10 μg/ml). Plates were developed using isotype-specific reagents conjugated with alkaline-phosphatase. White and grey columns show the values of respectively, preimmune and immune sera. Data represent means±the SD of 4 determinations conducted on 56-day serum samples from the responder animals depicted in the left panel.

Since the experimental results indicated that immunization with either the 9M peptide-KLH conjugate or pT.9M could induce significant serum bactericidal activity, it was next tested whether bactericidal titers could be further increased by priming with pT.9M followed by boosting with 9M-KLH. Bactericidal activity was observed in half of the animals after two administrations of pT.9M (FIG. 8a). In these responders (serum samples 1-4), but not in the non-responders (serum samples 5-8), boosting with 9M-KLH induced four to eight fold increases in serum bactericidal activity. These data indicate that DNA-priming followed by peptide boosting effectively increases bactericidal titers.

Isotype Specific of 9M-Induced Responses

The antibodies induced in animals primed with pT.9M and boosted with 9M-KLH were analyzed for their class/subclass distribution. After coating the plates with KLH-9M or with KLH alone, bound antibodies were revealed with isotype-specific reagents. A weak response was observed in plates coated with KLH alone, which could be totally inhibited by the addition of KLH in the reaction mixture (10 μg/ml; data not shown). FIG. 8b shows the reactivity of sera (diluted 1:100 in buffer containing 10 μg/ml of KLH) from animals primed with pT.9M followed by immunization with 9M-KLH. Anti-9M antibodies were mainly of the IgG class, with a predominance of IgG2a (FIGS. 8b, and 8c). In contrast, sera from animals undergoing gene vaccination alone (i.e. receiving p.T9M three times and no KLH-9M boost) showed either a prevalence of IgM or a mixed IgG response (data not shown). These data demonstrate that DNA priming followed by peptide boosting resulted in Th1 type antibody response.

Passive Immunoprotection

To further assess functional properties of the antibody responses induced by pT.9M immunization, we ascertained the ability of immune sera to passively protect infant rats from meningococcal bacteremia. Briefly, seven day-old Wistar rats (Charles River) were inoculated intraperitoneally with serially diluted mouse sera and, 2 h later, challenged intraperitoneally with $2 \times 10^3$ CFU of MenB (strain 2996). Blood samples were obtained 18 hours after challenge and the lowest plated dilution (1:10; 100 CFU/ml) was considered as the detection limit of the assay. Pups were considered protected from bacteremia in the presence of a sterile blood culture. In the experiments shown in Table 3, pups inoculated with up to a 1:4 dilution of a serum pool obtained from DNA-primed, peptide boosted animals were indeed protected from bacteremia. These data indicate that immunization with pT.9M induces serum antibodies having a protective activity in a well-characterized animal model of MenB infection.

TABLE 3

| Sample | CFU/ml (geometric mean)[a] | Number of protected rats/total |
|---|---|---|
| Seam 3 mAb, positive control (2 μg) | <100 | 4/4 |
| PBS | 46,062 | 0/5 |
| Preimmune serum pool diluted ½ | 4,124 | 0/8 |
| pCI (empty vector) Immune serum pool diluted ½ | 2,574 | 0/8 |
| pT.9M + 9M-KLH Immune serum pool diluted ½ | 104 | 6/8 |
| Immune serum pool diluted ¼ | 136 | 6/8 |
| Immune serum pool diluted ⅛ | 2,352 | 1/8 |

[a]For determination of geometric means, culture-negative animals were assigned an arbitrary value of 50 CFU/ml (i.e. half of 100 CFU/ml, the lower limit of detection).

REFERENCES (THE CONTENTS OF WHICH ARE HEREBY INCORPORATED IN FULL)

[1] Poolman et. al (1995) *Surface structures and secreted products of meningococci*. In K. Cartwright (ed.) *Meningococcal disease*. John Wiley & Sons, New York, N.Y. 21-34 pp.
[2] Rosenstien et al (2001) *Meningococcal disease*. N. Engl. J. Med. 344:1378-1388.
[3] Jennings, H. J. and Lugowski. C. (1981). *Immunochemistry of groups A, B, and C meningococcal polysaccharide-tetanus toxoid conjugates*. J. Immunol. 127:1011-1018.
[4] Finne et al. (1983). *Antigenic similarities between brain components and bacteria causing meningitis. Implications for vaccine development and pathogenesis*. Lancet. 2:355-357.
[5] Granoff et al. (1998). *Bactericidal monoclonal antibodies that define unique meningococcal B polysaccharide epitopes that do not cross-react with human polysialic acid*. J Immunol. 160:5028-5036.
[6] Shin et al. (2001). *Monoclonal antibodies specific for Neisseria meningitidis group B polysaccharide and their peptide mimotopes*. Infect. Immun. 69:3335-3342.
[7] Bodanszky (1993) *Principles of Peptide Synthesis* (ISBN: 0387564314).
[8] Fields et al. (1997) *Meth Enzymol* 289: *Solid-Phase Peptide Synthesis*. ISBN: 0121821900.
[9] Chan & White (2000) *Fmoc Solid Phase Peptide Synthesis*. ISBN: 0199637245.
[10] Kullmann (1987) *Enzymatic Peptide Synthesis*. ISBN: 0849368413.
[11] Ibba (1996) *Biotechnol Genet Eng Rev* 13:197-216.
[12] Kazmierski (1999) *Peptidomimetics Protocols*. ISBN: 0896035174.
[13] Abell (1999) *Advances in Amino Acid Mimetics and Peptidomimetics*. ISBN: 0762306149.
[14] U.S. Pat. No. 5,331,573 (Balaji).
[15] Goodman et al. (2001) *Biopolymers* 60:229-245.
[16] Hruby & Balse (2000) *Curr Med Chem* 7:945-970.
[17] Ribka & Rich (1998) *Curr Opin Chem Biol* 2:441-452.
[18] Chakraborty et al. (2002) *Curr Med Chem* 9:421-435.
[19] *Computer-Assisted Lead Finding and Optimization* (eds. Testra & Folkers, 1997).
[20] Available from Molecular Simulations Inc (http://www.msi.com/).
[21] Davie & Lawrence (1992) *Proteins* 12:31-41.
[22] Caflish et al. (1993) *J. Med. Chem.* 36:2142-67
[23] Eisen et al. (1994) *Proteins: Str. Funct. Genet.* 19:199-221.
[24] Böhm (1992) *J. Comp. Aided Molec. Design* 6:61-78.
[25] Gehlhaar et al. (1995) *J. Med. Chem.* 38:466-72.
[26] Moon & Howe (1991) *Proteins: Str. Funct. Genet.* 11:314-328.
[27] Available from http://chem.leeds.ac.uk/ICAMS/SPROUT.html.
[28] Lauri & Bartlett (1994) *Comp. Aided Mol. Design.* 8:51-66.
[29] Available from Tripos Inc (http://www.tripos.com).
[30] Rotstein et al. (1993) *J. Med. Chem.* 36:1700.
[31] Lai (1996) *J. Chem. Inf. Comput. Sci.* 36:1187-1194.
[32] Donnelly et al. (1997) *Annu Rev Immunol* 15:617-648.
[33] Strugnell et al. (1997) *Immunol Cell Biol* 75(4):364-369.
[34] Cui (2005) *Adv Genet.* 54:257-89.
[35] Robinson & Torres (1997) *Seminars in Immunol* 9:271-283.
[36] Brunham et al. (2000) *J Infect Dis* 181 Suppl 3:S538-43.
[37] Svanholm et al. (2000) *Scand J Immunol* 51(4):345-53.
[38] *DNA Vaccination—Genetic Vaccination* (1998) eds. Koprowski et al. (ISBN 3540633928).
[39] *Gene Vaccination: Theory and Practice* (1998) ed. Raz (ISBN 3540644288).
40 Prinz, D. M. et. al., *Immunology* (2003) 110:242-249
[41] Findeis et al., *Trends Biotechnol.* (1993) 11:202.
[42] Chiou et al. (1994) *Gene Therapeutics: Methods And Applications Of Direct Gene Transfer*. ed. Wolff.
[43] Wu et al., *J. Biol. Chem.* (1988) 263:621.

[44] Wu et al., *J. Biol. Chem.* (1994) 269:542.
[45] Zenke et al., *Proc. Natl. Acad. Sci.* (USA) (1990) 87:3655.
[46] Wu et al., *J. Biol. Chem.* (1991) 266:338.
[47] Jolly, *Cancer Gene Therapy* (1994) 1:51.
[48] Kimura, *Human Gene Therapy* (1994) 5:845.
[49] Connelly, *Human Gene Therapy* (1995) 1:185.
[50] Kaplitt, *Nature Genetics* (1994) 6:148.
[51] WO 90/07936.
[52] WO 94/03622.
[53] WO 93/25698.
[54] WO 93/25234.
[55] U.S. Pat. No. 5,219,740.
[56] WO 93/11230.
[57] WO 93/10218.
[58] U.S. Pat. No. 4,777,127.
[59] GB 2,200,651.
[60] EP-A-0 345 242.
[61] WO 91/02805.
[62] WO 94/12649.
[63] WO 93/03769.
[64] WO 93/19191.
[65] WO 94/28938.
[66] WO 95/11984.
[67] WO 95/00655.
[68] Curiel, *Hum. Gene Ther.* (1992) 3:147.
[69] Wu, *J. Biol. Chem.* (1989) 264:16985.
[70] U.S. Pat. No. 5,814,482.
[71] WO 95/07994.
[72] WO 96/17072.
[73] WO 95/30763.
[74] WO 97/42338.
[75] WO 90/11092.
[76] U.S. Pat. No. 5,580,859.
[77] U.S. Pat. No. 5,422,120.
[78] WO 95/13796.
[79] WO 94/23697.
[80] WO 91/14445.
[81] EP 0524968.
[82] Philip, *Mol. Cell. Biol.* (1994) 14:2411.
[83] Woffendin, *Proc. Natl. Acad. Sci.* (1994) 91:11581.
[84] U.S. Pat. No. 5,206,152.
[85] WO 92/11033.
[86] U.S. Pat. No. 5,149,655.
[87] WO 92/11033.
[88] Gennaro (2000) *Remington: The Science and Practice of Pharmacy.* 20th edition, ISBN: 0683306472.
[89] *Vaccine Design* . . . (1995) eds. Powell & Newman. ISBN: 030644867X. Plenum.
[90] WO00/23105.
[91] WO90/14837.
[92] Podda (2001) *Vaccine* 19:2673-80.
[93] Frey et al. (2003) *Vaccine* 21:4234-7.
[94] U.S. Pat. No. 6,299,884.
[95] U.S. Pat. No. 6,451,325.
[96] U.S. Pat. No. 5,057,540.
[97] WO96/33739.
[98] EP-A-0109942.
[99] WO96/11711.
[100] WO00/07621.
[101] Barr et al. (1998) *Advanced Drug Delivery Reviews* 32:247-271.
[102] Sjolanderet et al. (1998) *Advanced Drug Delivery Reviews* 32:321-338.
[103] Niikura et al. (2002) *Virology* 293:273-280.
[104] Lenz et al. (2001) *J Immunol* 166:5346-5355.
[105] Pinto et al. (2003) *J Infect Dis* 188:327-338.
[106] Gerber et al. (2001) *Virol* 75:4752-4760.
[107] WO03/024480
[108] WO03/024481
[109] Gluck et al. (2002) *Vaccine* 20:B10-B16.
[110] EP-A-0689454.
[111] Johnson et al. (1999) *Bioorg Med Chem Lett* 9:2273-2278.
[112] Evans et al. (2003) *Expert Rev Vaccines* 2:219-229.
[113] Meraldi et al. (2003) *Vaccine* 21:2485-2491.
[114] Pajak et al. (2003) *Vaccine* 21:836-842.
[115] Kandimalla et al. (2003) *Nucleic Acids Research* 31:2393-2400.
[116] WO02/26757.
[117] WO99/62923.
[118] Krieg (2003) *Nature Medicine* 9:831-835.
[119] McCluskie et al. (2002) *FEMS Immunology and Medical Microbiology* 32:179-185.
[120] WO98/40100.
[121] U.S. Pat. No. 6,207,646.
[122] U.S. Pat. No. 6,239,116.
[123] U.S. Pat. No. 6,429,199.
[124] Kandimalla et al. (2003) *Biochemical Society Transactions* 31 (part 3):654-658.
[125] Blackwell et al. (2003) *J Immunol* 170:4061-4068.
[126] Krieg (2002) *Trends Immunol* 23:64-65.
[127] WO01/95935.
[128] Kandimalla et al. (2003) *BBRC* 306:948-953.
[129] Bhagat et al. (2003) *BBRC* 300:853-861.
[130] WO03/035836.
[131] WO95/17211.
[132] WO98/42375.
[133] Beignon et al. (2002) *Infect Immun* 70:3012-3019.
[134] Pizza et al. (2001) *Vaccine* 19:2534-2541.
[135] Pizza et al. (2000) *Int J Med Microbiol* 290:455-461.
[136] Scharton-Kersten et al. (2000) *Inject Immun* 68:5306-5313.
[137] Ryan et al. (1999) *Infect Immun* 67:6270-6280.
[138] Partidos et al. (1999) *Immunol Lett* 67:209-216.
[139] Peppoloni et al. (2003) *Expert Rev Vaccines* 2:285-293.
[140] Pine et al. (2002) *J Control Release* 85:263-270.
[141] Domenighini et al. (1995) *Mol Microbiol* 15:1165-1167.
[142] WO99/40936.
[143] WO99/44636.
[144] Singh et al] (2001) *J Cont Release* 70:267-276.
[145] WO99/27960.
[146] U.S. Pat. No. 6,090,406
[147] U.S. Pat. No. 5,916,588
[148] EP-A-0626169.
[149] WO99/52549.
[150] WO01/21207.
[151] WO01/21152.
[152] Andrianov et al. (1998) *Biomaterials* 19:109-115.
[153] Payne et al. (1998) *Adv Drug Delivery Review* 31:185-196.
[154] Stanley (2002) *Clin Exp Dermatol* 27:571-577.
[155] Jones (2003) *Curr Opin Investig Drugs* 4:214-218.
[156] WO04/60308
[157] WO04/64759.
[158] WO99/11241.
[159] WO94/00153.
[160] WO98/57659.
[161] European patent applications 0835318, 0735898 and 0761231.
[162] WO03/009869.
[163] Costantino et al. (1992) *Vaccine* 10:691-698.
[164] Costantino et al. (1999) *Vaccine* 17:1251-1263.

[165] International patent application WO03/007985.
[166] Watson (2000) *Pediatr Infect Dis J* 19:331-332.
[167] Rubin (2000) *Pediatr Clin North Am* 47:269-285, v.
[168] Jedrzejas (2001) *Microbial Mol Biol Rev* 65:187-207.
[169] Bell (2000) *Pediatr Infect Dis J* 19:1187-1188.
[170] Iwarson (1995) *APMIS* 103:321-326.
[171] Gerlich et al. (1990) *Vaccine* 8 Suppl:S63-68 & 79-80.
[172] *Vaccines* (1988) eds. Plotkin & Mortimer. ISBN 0-7216-1946-0.
[173] Del Guidice et al. (1998) *Molecular Aspects of Medicine* 19:1-70.
[174] Gustafsson et al. (1996) *N. Engl. J. Med.* 334:349-355.
[175] Rappuoli et al. (1991) *TIBTECH* 9:232-238.
[176] Sutter et al. (2000) *Pediatr Clin North Am* 47:287-308.
[177] Zimmerman & Spann (1999) *Am Fam Physician* 59:113-118, 125-126.
[178] McMichael (2000) *Vaccine* 19 Suppl 1:S101-107.
[179] Schuchat (1999) *Lancet* 353(9146):51-6,
[180] International patent application WO02/34771.
[181] Dale (1999) *Infect Dis Clin North Am* 13:227-43, viii.
[182] Ferretti et al. (2001) *PNAS USA* 98: 4658-4663.
[183] Kuroda et al. (2001) *Lancet* 357(9264):1225-1240: see also pages 1218-1219.
[184] EP-A-0372501
[185] EP-A-0378881
[186] EP-A-0427347
[187] WO93/17712
[188] WO94/03208
[189] WO98/58668
[190] EP-A-0471177
[191] EP-A-0594610.
[192] WO00/56360
[193] WO91/01146
[194] WO00/61761
[195] WO01/72337
[196] Falugi et al. (2001) *Eur J Immunol* 31:3816-3824.
[197] Baraldo et al, (2004) *Infect Immun.* 72:4884-7
[198] WO02/091998.
[199] Kuo et al. (1995) *Infect Immun* 63:2706-13.
[200] *Research Disclosure*, 453077 (January 2002)
[201] Needleman & Wunsch (1970) *J. Mol. Biol.* 48, 443-453.
[202] Rice et al. (2000) *Trends Genet.* 16:276-277.
[203] Gennaro (2000) *Remington: The Science and Practice of Pharmacy.* 20th edition, ISBN: 0683306472.
[204] *Methods In Enzymology* (S. Colowick and N. Kaplan, eds., Academic Press, Inc.)
[205] *Handbook of Experimental Immunology*, Vols. I-IV (D. M. Weir and C. C. Blackwell, eds., 1986, Blackwell Scientific Publications)
[206] Sambrook, et al., *Molecular Cloning: A Laboratory Manual* (2nd Edition, 1989).
[207] *Handbook of Surface and Colloidal Chemistry* (Birdi, K. S. ed., CRC Press, 1997)
[208] *Short Protocols in Molecular Biology,* 4th ed. (Ausubel et al. eds., 1999, John Wiley & Sons)
[209] *Molecular Biology Techniques: An Intensive Laboratory Course,* (Ream et al., eds., 1998, Academic Press)
[210] *PCR (Introduction to Biotechniques Series),* 2nd ed. (Newton & Graham eds., 1997, Springer Verlag)

---

The invention claimed is:

1. A molecular mimetic of a unique epitope of *Neisseria meningitidis* serogroup B (MenB), wherein said mimetic is comprised of a peptide comprising an entire and contiguous amino acid sequence of one of SEQ ID NOs 1-13.

2. Nucleic acid encoding a polypeptide comprising an entire and contiguous amino acid sequence of one of SEQ ID NOs 1-13.

3. Nucleic acid comprising an entire and contiguous nucleotide sequence of one of SEQ ID NOs 18-32.

4. A vaccine composition comprising a peptide or nucleic acid molecule as claimed in any preceding claim in combination with a pharmaceutically acceptable carrier.

5. The vaccine composition of claim 4, wherein the peptide molecule comprises an entire and contiguous amino acid sequence of one of SEQ ID NOs 1-13.

6. The vaccine composition of claim 4 wherein said peptide molecule is covalently bound to a carrier molecule.

7. The vaccine composition of claim 4 further comprising an adjuvant.

8. The vaccine composition of claim 4, wherein the nucleic acid molecule comprises an entire and contiguous nucleotide sequence of one of SEQ ID NOs 18-32.

9. A pharmaceutical composition comprising the polypeptide of claim 1 or the nucleic acid of claim 2 or claim 3, in admixture with a pharmaceutically acceptable carrier.

10. A method for raising an immune response in a patient, comprising the step of administering the pharmaceutical composition of claim 9 to the patient.

11. A method as claimed in claim 10 comprising the steps of administering a pharmaceutical composition comprising a nucleic acid encoding a polypeptide comprising an entire and contiguous amino acid sequence of one of SEQ ID NOs 1-13 as a priming composition and a pharmaceutical composition comprising a polypeptide comprising an entire and contiguous amino acid sequence of one of SEQ ID NOs 1-13 as a boosting composition.

12. The method of claim 10, wherein the immune response is protective against *Neisseria meningitidis* serogroup B (MenB) infection.

13. A method for preventing *Neisseria meningitidis* serogroup B disease in a mammalian subject, said method comprising administering an effective amount of the vaccine of any one of claims 4-8 to said subject.

14. A method as claimed in claim 13, which method comprises administering an effective amount of the vaccine of claim 8 as a primer followed by administering an effective amount of the vaccine of claim 4 as a booster.

15. A method for treating or preventing *Neisseria meningitidis* serogroup B disease in a mammalian subject, said method comprising administering an effective amount of the pharmaceutical composition of claim 9 to said subject.

* * * * *

SEQUENCE LISTING

```
<160> NUMBER OF SEQ ID NOS: 38

<210> SEQ ID NO 1
<211> LENGTH: 12
<212> TYPE: PRT
<213> ORGANISM: Artificial Sequence
<220> FEATURE:
<223> OTHER INFORMATION: Synthesized Construct

<400> SEQUENCE: 1

Pro Pro Trp Asp Phe Asp Ala Gly Glu Gly Ile His
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Synthesized Construct

<400> SEQUENCE: 2

Asp Tyr Ala Trp Asp Asp Phe Tyr Ala Met Gly Asp
 1               5                  10

<210> SEQ ID NO 3
<211> LENGTH: 9
<212> TYPE: PRT
<213> ORGANISM: Artificial Sequence
<220> FEATURE:
<223> OTHER INFORMATION: Synthesized Construct

<400> SEQUENCE: 3

Asp Tyr Ala Trp Asp Gln Thr His Gln
 1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Synthesized Construct

<400> SEQUENCE: 4

Asp Tyr Ala Trp Asp Gln Thr His Gln
 1               5

<210> SEQ ID NO 5
<211> LENGTH: 9
<212> TYPE: PRT
<213> ORGANISM: Artificial Sequence
<220> FEATURE:
<223> OTHER INFORMATION: Synthesized Construct

<400> SEQUENCE: 5

Asp Tyr Ala Trp Asp Gln Thr His Gln
 1               5

<210> SEQ ID NO 6
<211> LENGTH: 9
<212> TYPE: PRT
<213> ORGANISM: Artificial Sequence
<220> FEATURE:
<223> OTHER INFORMATION: Synthesized Construct

<400> SEQUENCE: 6

Asp Ala Gly Asp Ser Gly Tyr Leu Thr
 1               5

<210> SEQ ID NO 7
<211> LENGTH: 9
<212> TYPE: PRT
<213> ORGANISM: Artificial Sequence
<220> FEATURE:
<223> OTHER INFORMATION: Synthesized Construct

<400> SEQUENCE: 7

Glu Phe Asp Ala Gly Asp Val Leu Leu
 1               5

<210> SEQ ID NO 8
<211> LENGTH: 9
<212> TYPE: PRT
<213> ORGANISM: Artificial Sequence
<220> FEATURE:
<223> OTHER INFORMATION: Synthesized Construct

<400> SEQUENCE: 8

Asp Ala Gly Asp His Ser His Pro Gln
 1               5

<210> SEQ ID NO 9
<211> LENGTH: 9
<212> TYPE: PRT
<213> ORGANISM: Artificial Sequence
<220> FEATURE:
<223> OTHER INFORMATION: Synthesized Construct

<400> SEQUENCE: 9

Asp Ala Gly Glu Val Tyr Pro Gly Pro
 1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Synthesized Construct

<400> SEQUENCE: 10

Asp Ala Gly Asp Ser Ala Tyr Ser Gln
 1               5

<210> SEQ ID NO 11
<211> LENGTH: 9
<212> TYPE: PRT
<213> ORGANISM: Artificial Sequence
<220> FEATURE:
<223> OTHER INFORMATION: Synthesized Construct

<400> SEQUENCE: 11

Asp Ala Gly Glu Gly Gly Pro Arg Val
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthesized Construct

<400> SEQUENCE: 12

Asp Ala Gly Glu Gly Gly Pro Arg Val
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthesized Construct

<400> SEQUENCE: 13

Asp Ala Gly Asp His Arg Ala Ala Ala
 1               5

<210> SEQ ID NO 14
<211> LENGTH: 20
<212> TYPE: PRT
<213> ORGANISM: Adenovirus E3 leader sequence

<400> SEQUENCE: 14

Met Arg Tyr Met Ile Leu Gly Leu Leu Ala Leu Ala Ala Val Cys Ser
 1               5                  10                  15

Ala Ala Glu Phe
            20

<210> SEQ ID NO 15
<211> LENGTH: 18
<212> TYPE: PRT
<213> ORGANISM: Adenovirus E3 leader sequence

<400> SEQUENCE: 15

Met Arg Tyr Met Ile Leu Gly Leu Leu Ala Leu Ala Ala Val Cys Ser
 1               5                  10                  15

Ala Ala

<210> SEQ ID NO 16
```

-continued

<211> LENGTH: 20
<212> TYPE: PRT
<213> ORGANISM: Tetanus toxoid T helper sequence

<400> SEQUENCE: 16

Met Lys Leu Gln Tyr Ile Lys Ala Asn Ser Lys Phe Ile Gly Ile Thr
1 5 10 15

Glu Leu Glu Phe
20

<210> SEQ ID NO 17
<211> LENGTH: 17
<212> TYPE: PRT
<213> ORGANISM: Tetanus toxoid T helper sequence

<400> SEQUENCE: 17

Gln Tyr Ile Lys Ala Asn Ser Lys Phe Ile Gly Ile Thr Glu Leu Glu
1 5 10 15

Phe

<210> SEQ ID NO 18
<211> LENGTH: 36
<212> TYPE: DNA
<213> ORGANISM: Artificial Sequence
<220> FEATURE:
<223> OTHER INFORMATION: Synthesized Construct

<400> SEQUENCE: 18
ccgccgtggg acttcgacgc gggtgaaggt atccac 36

<210> SEQ ID NO 19
<211> LENGTH: 36
<212> TYPE: DNA
<213> ORGANISM: Artificial Sequence
<220> FEATURE:
<223> OTHER INFORMATION: Synthesized Construct

<400> SEQUENCE: 19
ccaccttggg atttcgatgc cggcgagggc attcac 36

<210> SEQ ID NO 20
<211> LENGTH: 36
<212> TYPE: DNA
<213> ORGANISM: Artificial Sequence
<220> FEATURE:
<223> OTHER INFORMATION: Synthesized Construct

<400> SEQUENCE: 20
gactacgcgt gggacgactt ctacgcgatg ggggat 36

<210> SEQ ID NO 21
<211> LENGTH: 36
<212> TYPE: DNA
<213> ORGANISM: Artificial Sequence
<220> FEATURE:
<223> OTHER INFORMATION: Synthesized Construct

<400> SEQUENCE: 21
gattatgcat gggatgactt ctacgctatg ggtgac 36

<210> SEQ ID NO 22
<211> LENGTH: 27
<212> TYPE: DNA
<213> ORGANISM: Artificial Sequence
<220> FEATURE:
<223> OTHER INFORMATION: Synthesized Construct

```
<400> SEQUENCE: 22
gattacgcat gggaccaaac ccattag                                       27

<210> SEQ ID NO 23
<211> LENGTH: 27
<212> TYPE: DNA
<213> ORGANISM: Artificial Sequence
<220> FEATURE:
<223> OTHER INFORMATION: Synthesized Construct

<400> SEQUENCE: 23
gattatgcct gggatcagac tcaccag                                       27

<210> SEQ ID NO 24
<211> LENGTH: 27
<212> TYPE: DNA
<213> ORGANISM: Artificial Sequence
<220> FEATURE:
<223> OTHER INFORMATION: Synthesized Construct

<400> SEQUENCE: 24
gatgctggcg actctggcta tttgacg                                       27

<210> SEQ ID NO 25
<211> LENGTH: 27
<212> TYPE: DNA
<213> ORGANISM: Artificial Sequence
<220> FEATURE:
<223> OTHER INFORMATION: Synthesized Construct

<400> SEQUENCE: 25
gatgccggcg attctggcta tctgact                                       27

<210> SEQ ID NO 26
<211> LENGTH: 27
<212> TYPE: DNA
<213> ORGANISM: Artificial Sequence
<220> FEATURE:
<223> OTHER INFORMATION: Synthesized Construct

<400> SEQUENCE: 26
gagttcgatg cgggtgacgt gttgctg                                       27

<210> SEQ ID NO 27
<211> LENGTH: 27
<212> TYPE: DNA
<213> ORGANISM: Artificial Sequence
<220> FEATURE:
<223> OTHER INFORMATION: Synthesized Construct

<400> SEQUENCE: 27
gacgctgggg accattcgca tccgcag                                       27

<210> SEQ ID NO 28
<211> LENGTH: 27
<212> TYPE: DNA
<213> ORGANISM: Artificial Sequence
<220> FEATURE:
<223> OTHER INFORMATION: Synthesized Construct

<400> SEQUENCE: 28
gatgccggcg atcactctca cccacag                                       27

<210> SEQ ID NO 29
<211> LENGTH: 27
```

```
<212> TYPE: DNA
<213> ORGANISM: Artificial Sequence
<220> FEATURE:
<223> OTHER INFORMATION: Synthesized Construct

<400> SEQUENCE: 29
gatgctgggg aagtatatcc aggtccg                                          27

<210> SEQ ID NO 30
<211> LENGTH: 27
<212> TYPE: DNA
<213> ORGANISM: Artificial Sequence
<220> FEATURE:
<223> OTHER INFORMATION: Synthesized Construct

<400> SEQUENCE: 30
gacgccggcg attcggcgta ctcccag                                          27

<210> SEQ ID NO 31
<211> LENGTH: 27
<212> TYPE: DNA
<213> ORGANISM: Artificial Sequence
<220> FEATURE:
<223> OTHER INFORMATION: Synthesized Construct

<400> SEQUENCE: 31
gatgcgggcg agggcgggcc acgcgtg                                          27

<210> SEQ ID NO 32
<211> LENGTH: 27
<212> TYPE: DNA
<213> ORGANISM: Artificial Sequence
<220> FEATURE:
<223> OTHER INFORMATION: Synthesized Construct

<400> SEQUENCE: 32
gacgcaggcg atcatcgcgc ggcggcg                                          27

<210> SEQ ID NO 33
<211> LENGTH: 13
<212> TYPE: PRT
<213> ORGANISM: Artificial Sequence
<220> FEATURE:
<223> OTHER INFORMATION: Synthesized Construct

<400> SEQUENCE: 33

Asp Tyr Ala Trp Asp Gln Thr His Gln Asp Pro Ala Lys
 1               5                  10

<210> SEQ ID NO 34
<211> LENGTH: 17
<212> TYPE: PRT
<213> ORGANISM: Artificial Sequence
<220> FEATURE:
<223> OTHER INFORMATION: Synthesized Construct

<400> SEQUENCE: 34

Pro Pro Trp Asp Phe Asp Ala Gly Glu Gly Ile His Gly Asp Pro Ala
 1               5                  10                  15

Lys

<210> SEQ ID NO 35
<211> LENGTH: 60
<212> TYPE: DNA
<213> ORGANISM: Adenovirus E3 leader sequence

<400> SEQUENCE: 35
```

```
atgaggtaca tgattttagg cttgctcgcc cttgcggcag tctgcagcgc tgccgaattc        60

<210> SEQ ID NO 36
<211> LENGTH: 54
<212> TYPE: DNA
<213> ORGANISM: Adenovirus E3 leader sequence

<400> SEQUENCE: 36
atgaggtaca tgattttagg cttgctcgcc cttgcggcag tctgcagcgc tgcc             54

<210> SEQ ID NO 37
<211> LENGTH: 60
<212> TYPE: DNA
<213> ORGANISM: Tetanus toxoid T helper sequence

<400> SEQUENCE: 37
atgaaactac agtatataaa agcaaattct aaatttatag gtataactga actagaattc       60

<210> SEQ ID NO 38
<211> LENGTH: 51
<212> TYPE: DNA
<213> ORGANISM: Tetanus toxoid T helper sequence

<400> SEQUENCE: 38
cagtatataa aagcaaattc taaatttata ggtataactg aactagaatt c                51
```